(12) United States Patent
Hoekman et al.

(10) Patent No.: US 9,919,117 B2
(45) Date of Patent: Mar. 20, 2018

(54) NOZZLES FOR NASAL DRUG DELIVERY

(71) Applicant: Impel NeuroPharma Inc., Seattle, WA (US)

(72) Inventors: John D. Hoekman, Seattle, WA (US); Michael Hite, Normandy Park, WA (US); Alan Brunelle, Woodinville, WA (US); Joel Relethford, Everett, WA (US)

(73) Assignee: IMPEL NEUROPHARMA INC., Seattle, WA (US)

( * ) Notice: Subject to any disclaimer, the term of this patent is extended or adjusted under 35 U.S.C. 154(b) by 312 days.

(21) Appl. No.: 14/075,126

(22) Filed: Nov. 8, 2013

(65) Prior Publication Data

US 2014/0083424 A1    Mar. 27, 2014

Related U.S. Application Data

(63) Continuation of application No. PCT/US2012/037132, filed on May 9, 2012.
(Continued)

(51) Int. Cl.
*A61M 15/08* (2006.01)
*A61M 15/00* (2006.01)
(Continued)

(52) U.S. Cl.
CPC ........ *A61M 15/08* (2013.01); *A61M 15/0021* (2014.02); *A61M 16/127* (2014.02); *B05B 1/14* (2013.01); *B05B 7/08* (2013.01); *A61M 16/208* (2013.01); *A61M 2202/064* (2013.01); *A61M 2210/0612* (2013.01); *A61M 2210/0618* (2013.01); *A61M 2210/1067* (2013.01); *A61M 2210/1475* (2013.01)

(58) Field of Classification Search
CPC ............ A61M 15/08; A61M 2202/064; A61M 2210/0618; A61M 15/0001; B05B 1/14; B05B 7/08
USPC .......................... 128/203.22, 200.14, 200.23
See application file for complete search history.

(56) References Cited

U.S. PATENT DOCUMENTS

| 2,933,259 A | 4/1960 | Raskin |
| 3,425,414 A | 2/1969 | Laroche |

(Continued)

FOREIGN PATENT DOCUMENTS

| CN | 1293580 | 5/2001 |
| CN | 1930054 | 3/2007 |

(Continued)

OTHER PUBLICATIONS

Spraying Systems, "Technical Reference" Jun. 25th, 2006, p. A5.*
(Continued)

*Primary Examiner* — Peter S Vasat
*Assistant Examiner* — Margaret Luarca
(74) *Attorney, Agent, or Firm* — Fenwick & West LLP

(57) ABSTRACT

A nozzle for use in delivering a mixture of aerosol propellant and drug formulation. The nozzle includes a drug product inlet configured to receive a mixture of aerosolized propellant and an intranasal dosage form. The inlet is disposed at the proximal end. A nozzle body is secured to the drug product inlet. Two or more channels are disposed within the body. Two or more orifice apertures are disposed at the distal end of the nozzle.

14 Claims, 31 Drawing Sheets

Related U.S. Application Data

(60) Provisional application No. 61/484,048, filed on May 9, 2011.

(51) Int. Cl.
*A61M 16/12* (2006.01)
*B05B 7/08* (2006.01)
*B05B 1/14* (2006.01)
*A61M 16/20* (2006.01)

(56) References Cited

U.S. PATENT DOCUMENTS

| | | | |
|---|---|---|---|
| 3,767,125 A * | 10/1973 | Gehres | B05B 1/14 239/552 |
| 3,888,253 A | 6/1975 | Wall et al. | |
| 3,906,950 A | 9/1975 | Cocozza | |
| 3,908,654 A | 9/1975 | Lhoest et al. | |
| 3,921,637 A | 11/1975 | Bennie et al. | |
| 3,949,939 A | 4/1976 | Brown | |
| 3,971,377 A | 7/1976 | Damani | |
| 3,998,226 A | 12/1976 | Harris | |
| 4,095,596 A | 6/1978 | Grayson | |
| 4,187,985 A | 2/1980 | Goth | |
| 4,227,522 A | 10/1980 | Carris | |
| 4,338,931 A | 7/1982 | Cavazza | |
| 4,353,365 A | 10/1982 | Hallworth et al. | |
| 4,412,573 A | 11/1983 | Zdeb | |
| 4,446,990 A | 5/1984 | Stevenson et al. | |
| 4,620,670 A | 11/1986 | Hughes | |
| 4,702,415 A | 10/1987 | Hughes | |
| 4,896,832 A | 1/1990 | Howlett | |
| 4,995,385 A | 2/1991 | Valentini et al. | |
| 5,170,942 A | 12/1992 | Spink et al. | |
| 5,224,471 A | 7/1993 | Marelli et al. | |
| 5,307,953 A | 5/1994 | Regan | |
| 5,331,954 A | 7/1994 | Rex et al. | |
| 5,349,947 A | 9/1994 | Newhouse et al. | |
| 5,382,236 A | 1/1995 | Otto et al. | |
| 5,398,850 A | 3/1995 | Sancoff et al. | |
| 5,435,282 A | 7/1995 | Haber et al. | |
| 5,505,193 A | 4/1996 | Ballini et al. | |
| 5,516,006 A | 5/1996 | Meshberg | |
| 5,690,256 A * | 11/1997 | Smith | B65D 83/206 222/402.1 |
| 5,711,488 A | 1/1998 | Lund | |
| 5,715,811 A | 2/1998 | Ohki et al. | |
| 5,797,390 A | 8/1998 | McSoley | |
| 5,814,020 A | 9/1998 | Gross | |
| 5,819,730 A | 10/1998 | Stone et al. | |
| 5,823,183 A | 10/1998 | Casper et al. | |
| 5,875,776 A | 3/1999 | Vaghefi | |
| 5,881,719 A | 3/1999 | Gottenauer et al. | |
| 5,901,703 A | 5/1999 | Ohki et al. | |
| 5,906,198 A | 5/1999 | Flickinger | |
| 5,910,301 A | 6/1999 | Farr et al. | |
| 5,954,696 A | 9/1999 | Ryan | |
| 6,062,213 A | 5/2000 | Fuisz et al. | |
| 6,092,522 A | 7/2000 | Calvert et al. | |
| 6,145,703 A | 11/2000 | Opperman | |
| 6,158,676 A * | 12/2000 | Hughes | A61M 11/06 239/337 |
| 6,180,603 B1 | 1/2001 | Frey, II | |
| 6,186,141 B1 | 2/2001 | Pike et al. | |
| 6,189,739 B1 | 2/2001 | von Schuckmann | |
| 6,294,153 B1 | 9/2001 | Modi | |
| 6,302,101 B1 | 10/2001 | Py | |
| 6,313,093 B1 | 11/2001 | Frey, II | |
| 6,347,789 B1 | 2/2002 | Rock | |
| 6,367,471 B1 | 4/2002 | Genosar et al. | |
| 6,367,473 B1 | 4/2002 | Kafer | |
| 6,382,465 B1 | 5/2002 | Greiner-Perth | |
| 6,410,046 B1 | 6/2002 | Lermer | |
| 6,418,925 B1 | 7/2002 | Genova et al. | |
| 6,491,940 B1 | 12/2002 | Levin | |
| 6,540,983 B1 | 4/2003 | Adjei et al. | |
| 6,569,463 B2 | 5/2003 | Patel et al. | |
| 6,585,172 B2 | 7/2003 | Arghyris | |
| 6,585,957 B1 | 7/2003 | Adjei et al. | |
| 6,585,958 B1 | 7/2003 | Keller et al. | |
| 6,595,202 B2 | 7/2003 | Ganan-Calvo | |
| 6,622,721 B2 | 9/2003 | Vedrine et al. | |
| 6,644,305 B2 | 11/2003 | MacRae et al. | |
| 6,644,309 B2 | 11/2003 | Casper et al. | |
| 6,647,980 B1 | 11/2003 | Gizurarson | |
| 6,681,767 B1 | 1/2004 | Patton et al. | |
| 6,684,879 B1 | 2/2004 | Coffee et al. | |
| 6,701,916 B2 | 3/2004 | Mezzoli | |
| 6,715,485 B1 | 4/2004 | Djupesland | |
| 6,729,334 B1 * | 5/2004 | Baran | A61M 16/0463 128/200.14 |
| 6,734,162 B2 | 5/2004 | Van Antwerp et al. | |
| 6,810,872 B1 | 11/2004 | Ohki et al. | |
| 6,923,988 B2 | 8/2005 | Patel et al. | |
| 6,991,785 B2 | 1/2006 | Frey, II | |
| 7,033,598 B2 | 4/2006 | Lemer | |
| 7,051,734 B2 | 5/2006 | Casper et al. | |
| 7,063,686 B2 | 6/2006 | Mezzoli | |
| 7,163,013 B2 | 1/2007 | Harrison | |
| 7,182,277 B2 | 2/2007 | Vedrine et al. | |
| 7,200,432 B2 | 4/2007 | Lemer et al. | |
| 7,214,209 B2 | 5/2007 | Mazzoni | |
| 7,231,919 B2 | 6/2007 | Giroux | |
| 7,258,119 B2 | 8/2007 | Mazzoni | |
| 7,296,566 B2 | 11/2007 | Alchas | |
| 7,347,201 B2 | 3/2008 | Djupesland | |
| 7,377,901 B2 | 5/2008 | Djupesland et al. | |
| 7,476,689 B2 | 1/2009 | Santus et al. | |
| 7,481,218 B2 | 1/2009 | Djupesland | |
| 7,543,581 B2 | 6/2009 | Djupesland | |
| 7,655,619 B2 | 2/2010 | During et al. | |
| 7,740,014 B2 | 6/2010 | Djupesland | |
| 7,784,460 B2 | 8/2010 | Djupesland et al. | |
| 7,799,337 B2 | 9/2010 | Levin | |
| 7,819,342 B2 | 10/2010 | Spallek et al. | |
| 7,832,394 B2 | 11/2010 | Schechter et al. | |
| 7,841,337 B2 | 11/2010 | Djupesland | |
| 7,841,338 B2 | 11/2010 | Dunne et al. | |
| 7,854,227 B2 | 12/2010 | Djupesland | |
| 7,866,316 B2 | 1/2011 | Giroux | |
| 7,875,001 B2 | 1/2011 | Minotti | |
| 7,905,229 B2 | 3/2011 | Giroux et al. | |
| 7,934,503 B2 | 5/2011 | Djupesland et al. | |
| 7,975,690 B2 | 7/2011 | Djupesland | |
| 7,994,197 B2 | 8/2011 | Cook et al. | |
| 8,001,963 B2 | 8/2011 | Giroux | |
| 8,047,202 B2 | 11/2011 | Djupesland | |
| 8,119,639 B2 | 2/2012 | Cook et al. | |
| 8,122,881 B2 | 2/2012 | Giroux | |
| 8,146,589 B2 | 4/2012 | Djupesland | |
| 8,171,929 B2 | 5/2012 | Djupesland et al. | |
| 8,327,844 B2 | 12/2012 | Djupesland | |
| 8,408,427 B2 | 4/2013 | Wong | |
| 8,448,637 B2 | 5/2013 | Giroux | |
| 8,511,303 B2 | 8/2013 | Djupesland | |
| 8,517,026 B2 | 8/2013 | Amon | |
| 8,522,778 B2 | 9/2013 | Djupesland | |
| 8,550,073 B2 * | 10/2013 | Djupesland | A61M 11/00 128/200.23 |
| 8,555,877 B2 | 10/2013 | Djupesland | |
| 8,555,878 B2 | 10/2013 | Djupesland | |
| 8,596,278 B2 | 12/2013 | Djupesland | |
| 8,733,342 B2 | 5/2014 | Giroux et al. | |
| 8,757,146 B2 | 6/2014 | Hoekman et al. | |
| 8,800,555 B2 | 8/2014 | Djupesland | |
| 8,839,790 B2 | 9/2014 | Beck Arnon | |
| 8,875,794 B2 | 11/2014 | Carlsen et al. | |
| 8,899,229 B2 | 12/2014 | Djupesland et al. | |
| 8,899,230 B2 | 12/2014 | Immel | |
| 8,910,629 B2 | 12/2014 | Djupesland et al. | |
| 8,925,544 B2 | 1/2015 | Flickinger | |
| 8,978,647 B2 | 3/2015 | Djupesland et al. | |
| 8,987,199 B2 | 3/2015 | Abdel Maksoud et al. | |
| 9,010,325 B2 | 4/2015 | Djupesland et al. | |

(56) References Cited

U.S. PATENT DOCUMENTS

| | | |
|---|---|---|
| 9,038,630 B2 | 5/2015 | Djupesland et al. |
| 9,067,034 B2 | 6/2015 | Djupesland et al. |
| 9,072,857 B2 | 7/2015 | Djupesland |
| 9,101,539 B2 | 8/2015 | Nagata et al. |
| 9,119,932 B2 | 9/2015 | Djupesland |
| 9,180,264 B2 | 11/2015 | Young et al. |
| 9,272,104 B2 | 3/2016 | Djupesland |
| 9,446,207 B2 | 9/2016 | Jung |
| 2002/0017294 A1 | 2/2002 | Py |
| 2002/0054856 A1 | 5/2002 | Jones |
| 2002/0092520 A1 | 7/2002 | Casper et al. |
| 2002/0132803 A1* | 9/2002 | Dedhiya ............ A61K 9/0043 514/182 |
| 2003/0017119 A1 | 1/2003 | Rabinowitz et al. |
| 2003/0158527 A1 | 8/2003 | Mezzoli |
| 2003/0217748 A1 | 11/2003 | Giroux |
| 2004/0025866 A1 | 2/2004 | Vedrine et al. |
| 2004/0068222 A1 | 4/2004 | Brian |
| 2004/0094146 A1 | 5/2004 | Schiewe et al. |
| 2004/0238574 A1 | 12/2004 | Merk et al. |
| 2005/0023376 A1 | 2/2005 | Anderson |
| 2005/0028812 A1 | 2/2005 | Djupesland |
| 2005/0036985 A1 | 2/2005 | Ensoli |
| 2005/0098172 A1 | 5/2005 | Anderson |
| 2005/0142072 A1 | 6/2005 | Birch et al. |
| 2005/0274378 A1 | 12/2005 | Bonney et al. |
| 2006/0107957 A1 | 5/2006 | Djupesland |
| 2006/0219813 A1 | 10/2006 | Morrison |
| 2006/0240092 A1 | 10/2006 | Breitenkamp et al. |
| 2006/0260608 A1 | 11/2006 | Armstrong et al. |
| 2007/0056585 A1 | 3/2007 | Davies et al. |
| 2007/0068514 A1 | 3/2007 | Giroux |
| 2007/0074722 A1 | 4/2007 | Giroux et al. |
| 2007/0119451 A1 | 5/2007 | Wang et al. |
| 2007/0131224 A1 | 6/2007 | Giroux |
| 2007/0172517 A1 | 7/2007 | Ben-Sasson et al. |
| 2007/0202051 A1 | 8/2007 | Schuschnig |
| 2008/0054099 A1 | 3/2008 | Giroux et al. |
| 2008/0163874 A1 | 7/2008 | Djupesland |
| 2008/0178871 A1 | 7/2008 | Genova et al. |
| 2008/0230053 A1* | 9/2008 | Kraft ............ A61M 11/06 128/200.23 |
| 2008/0305077 A1 | 12/2008 | Frey, II et al. |
| 2009/0320832 A1 | 12/2009 | Djupestand |
| 2010/0074959 A1 | 3/2010 | Hansom et al. |
| 2010/0218759 A1 | 9/2010 | Anderson et al. |
| 2011/0045088 A1 | 2/2011 | Tsutsui et al. |
| 2011/0048414 A1 | 3/2011 | Hoekman et al. |
| 2011/0053859 A1 | 3/2011 | Deadwyler et al. |
| 2012/0195959 A1 | 8/2012 | Ishii |
| 2012/0222675 A1 | 9/2012 | Dunne et al. |
| 2014/0170220 A1 | 6/2014 | Cartt et al. |
| 2014/0343494 A1 | 11/2014 | Hoekman et al. |
| 2015/0057287 A1 | 2/2015 | Cook et al. |
| 2015/0216823 A1 | 8/2015 | Chatterjee |
| 2015/0258178 A1 | 9/2015 | Gong |
| 2016/0101245 A1 | 4/2016 | Hoekman et al. |
| 2016/0228433 A1 | 8/2016 | Haruta et al. |

FOREIGN PATENT DOCUMENTS

| | | |
|---|---|---|
| CN | 101528358 | 9/2009 |
| DE | 19518580 A1 | 11/1996 |
| DE | 102013100473 A1 | 7/2014 |
| EP | 0692273 | 1/1996 |
| EP | 1165044 A2 | 1/2002 |
| GB | 806284 A | 12/1958 |
| GB | 1517642 A | 7/1978 |
| JP | 838607 | 2/1996 |
| JP | H08280808 | 10/1996 |
| JP | H08322934 A | 12/1996 |
| JP | H09135901 | 5/1997 |
| JP | H09248342 | 9/1997 |
| JP | 2000217919 | 8/2000 |
| JP | 2005537834 | 12/2005 |
| JP | 2007535352 | 12/2007 |
| JP | 2010501227 | 1/2010 |
| JP | 2010501228 | 1/2010 |
| JP | 2011511674 | 4/2011 |
| WO | WO8601731 A1 | 3/1986 |
| WO | WO9629044 A1 | 9/1996 |
| WO | WO9913930 A1 | 3/1999 |
| WO | WO0054887 A1 | 9/2000 |
| WO | WO0136033 A2 | 5/2001 |
| WO | WO0209707 | 2/2002 |
| WO | WO2007/012853 A1 | 2/2007 |
| WO | WO2008/059385 A2 | 5/2008 |
| WO | WO2009100383 A2 | 8/2009 |
| WO | WO2012072542 | 6/2012 |
| WO | WO2012119153 | 9/2012 |

OTHER PUBLICATIONS

The PCT Search Report and Written Opinion dated Jul. 26, 2012 for PCT application No. PCT/US12/37132, 9 pages.

PCT Application PCT/US11/48435, filed on Aug. 19, 2011, Hoekman et al, Circumferential Aerosol Device for Delivering Drugs to Olfactory Epithelium and Brain.

The Extended EP Search Report dated Nov. 28, 2014 for European patent application No. 12781605.6, 10 pages.

The PCT Search Report and Written Opinion dated Aug. 14, 2014 for PCT application No. PCT/US14/35711, 13 pages.

Translated Chinese Office Action dated Sep. 9, 2015 for Chinese patent application No. 201280029975.6, a counterpart foreign application of U.S. Appl. No. 14/075,126, 39 pages.

Banks, et al., "Brain Uptake of the Glucagon-Like Peptide-1 Antagonist Exendin(9-39) After Intranasal Administration", J. Pharmacol. Exp. Ther., 2004, vol. 309 (2), pp. 469-475.

Translated Chinese Office Action dated May 24, 2016 for Chinese patent application No. 21280029975.6, a counterpart foreign application of U.S. Appl. No. 14/075,126, 38 pages.

Ding, et al., "Olfactory Mucosa: Composition, Enzymatic Localization, and Metabolism", Handbook of Olfaction and Gustation, 2nd Ed (Doty RL, Ed), 2003, pp. 51-73.

Guo, et al., "Evaluation of Impaction Force of Nasal Sprays and Metered-Dose Inhalers Using the Texture Analyser", J. Pharm. Sci., 2009, vol. 98 (8), pp. 2799-2806.

Henry, et al., "A Pharmacokinetic Study of Midazolam in Dogs: Nasal Drop vs. Atomizer Administration", Pediatr. Dent, 1998, vol. 20 (5), pp. 321-326.

Translated Japanese Office Action dated Apr. 5, 2016 for Japanese Patent Application No. 2014-510444, a counterpart foreign application of U.S. Appl. No. 14/075,126, 25 pages.

Letrent, et al., "Effects of a Potent and Specific P-Glycoprotein Inhibitor on the Blood-Brain Barrier Distribution and Antinociceptive Effect of Morphine in the Rat", Drug Metab. Dispos., 1991, vol. 27 (7), pp. 827-834.

Liu, et al., "Creation of a Standardized Geometry of the Human Nasal Cavity", J. Appl. Physiol., 2009, vol. 106 (3), pp. 784-795.

Mathison, et al., "Nasal Route for Direct Delivery of Solutes to the Central Nervous System: Fact or Fiction?", J. Drug Target, 1998, vol. 5 (6), pp. 415-441.

Morrison, et al., "Morphology of the Human Olfactory Epithelium", J. Comp. Neurol., 1990, vol. 297 (1), pp. 1-13.

Pardridge, "Targeting Neurotherapeutic Agents through the Blood-Brain Barrier", Arch. Neurol., 2002, vol. 59 (1), pp. 35-40.

Pardridge, "The Blood-Brain Barrier: Bottleneck in Brain Drug Development", NeuroRx., 2005, vol. 2 (1), pp. 3-14.

Pardridge, "The Blood-Brain Barrier and Neurotherapeutics", NeuroRx., 2005, vol. 2 (1), pp. 1-2.

Petroianu, et al., "New K-Oximes (K-27 and K-48) in Comparison with Obidoxime (LuH-6), HI-6, Trimedoxime (TMB-4), and Pralidoxime (2-PAM): Survival in Rats Exposed IP to the Organophosphate Paraoxon", Toxicol. Mech. Methods, 2007, vol. 17 (7), pp. 401-408.

(56) References Cited

OTHER PUBLICATIONS

Translated Russian Office Action dated Apr. 26, 2016 for Russian Patent Application No. 2013154420, a counterpart foreign application of U.S. Appl. No. 14/075,126, 6 pages.
Sakane, et al., "Transport of Cephalexin to the Cerebrospinal Fluid Directly from the Nasal Cavity", J. Pharm. Pharmacol., 1991, vol. 43 (6), pp. 449-451.
Thiermann, et al., "Pharmacokinetics of Obidoxime in Patients Poisoned with Organophosphorus Compounds" Toxicol. Lett., 2010, vol. 197 (3), pp. 236-242.
Zhang et al., "Preparation of Nimodipine-Loaded Microemulsion for Intranasal Delivery and Evaluation on the Targeting Efficiency to the Brain", Int. J. Pharm., 2004, vol. 275 (1-2), pp. 85-96.
Appasaheb, et al., "Review on Intranasal Drug Delilvery System", Journal of Advanced Pharmacy Education and Research, vol. 3, Issue 4, Oct. 2013, 14 pages.
The Australian Office Action dated Jan. 23, 2017 for Australian patent application No. 2012253569, a counterpart foreign application of U.S. Appl. No. 14/075,126, 3 pages.
Baron, "Orally Inhaled Dihydroergotamine; Reviving and Improving a Classic", Future Neurology, May 2011, 11 pages.
Translated Chinese Office Action dated Jan. 18, 2017 for Chinese Patent Application No. 21280029975.6, a counterpart foreign application of U.S. Appl. No. 14/075,126, 6 pages.
Constantino, et al., "Intranasal administration of acetylcholinesterase inhibitors", BMC Neuroscience, Dec. 10, 2008, 3 pages.
EP Ofice Action for 14727320.5, dated Nov. 9, 2016, 6 pages.
EP Search Report for 09707800.0 dated Jul. 1, 2015, 12 pages.
EP Search Report for 11818832.5 dated Sep. 24, 2014, 6 pages.
Hanson, et al., "Intranasal delivery of growth differentiation factor 5 to the central nervous system", Drug Delivery, 19(3):149-54, Feb. 2012, 7 pages.
Hoekman, J.D., "The Impact of Enhanced Olfactory Deposition and Retention on Direct Nose-to-Brain Drug Delivery", UMI Dissertation Publishing, Apr. 11, 2011, 181 pages.
International Search Report for PCT/US/2009/033468 dated Dec. 2, 2009, 5 pages.
Kumar, et al., "Nasal Drug Delivery: A Potential Route for Brain Targeting" The Pharma Innovation Journal, vol. 2, No. 1, Mar. 2013. 9 pages.
Ozsoy, et al., "Nasal Delivery of High Molecular Weight Drugs", Molecules Journal, Sep. 23, 2009, 26 pages.
Parvathi, "Intranasal Drug Delivery to Brain: An Overview," published in the International Journal of Research in Pharmacy and Chemistry 2012, 2(3), 7 pages.
The PCT Search Report and Written Opinion dated Mar. 27, 2012 for PCT application No. PCT/US11/48435, 14 pages.
Renner, et al., "Intranasal delivery of growth differentiation factor 5 to the central nervous system," Drug Delivery, Feb. 2012, 7 pages.
Translated Russian Office Action dated Aug. 18, 2016 for Russian patent application No. 2013154420, a counterpart foreign application of U.S. Appl. No. 14/075,126, 6 pages.
Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, vol. 39, No. 12, 8 pages.
Talegaonkar, et al., "Intranasal delivery: an approach to bypass the blook brain barrier", Indian J Pharmacol, Jun. 2004, vol. 36, Issue 3, 8 pages.
Westin et al, "Direct Nose to Brain Transfer of Morphine After Nasal Administration to Rats", Pharmaceutical Research, vol. 23, No. 3, Mar. 2006, 8 pgs.
Westin, "Olfactory Tranfser of Analgesic Drugs After Nasal Administration", Digital Comprehensive Summaries of Uppsala Dissertations from the Faculty of Pharmacy 55, May 11, 2007, 66 pages.
Yamada, et al., "Nose-to-brain delivery of TS-002, prostaglandin D2 analogue", Journal of Drug Targeting, Jan. 2007, 9 pages.
Yiman, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medecine, 3(1), Jan. 2008, 4 pages.
Zhang, et al, "The brain targeting efficiency following nasally applied MPEG-PLA nanoparticles in rats", Journal of Drug Targeting, Jun. 2006, 11 pages.
Translated Japanese Office Action dated Mar. 28, 2017 for Japanese patent application No. 2014-510444, a counterpart foreign application of U.S. Appl. No. 14/075,126, 7 pages.
The Japanese Reexamination Report dated Aug. 29, 2017 for Japanese patent application No. 2014-51044.4, a counterpart foreign application of U.S. Appl. No. 14/075,126, 6 pages.
The European Office Action dated Aug. 16, 2017 for European patent application No. 12781605.6, a counterpart foreign application of U.S. Appl. No. 14/075,126, 5 pages.
The Australian Office Action dated Dec. 4, 2017 for Australian patent application No. 2012253569, a counterpart foreign application of U.S. Appl. No. 14/075,126, 5 pages.

* cited by examiner

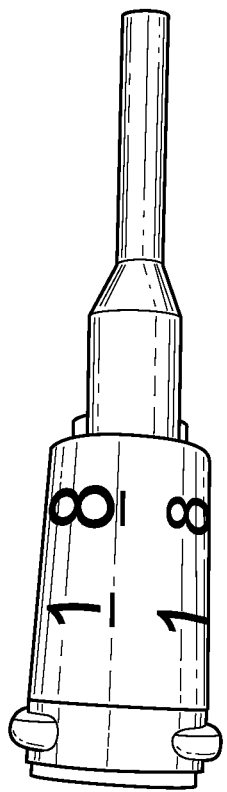
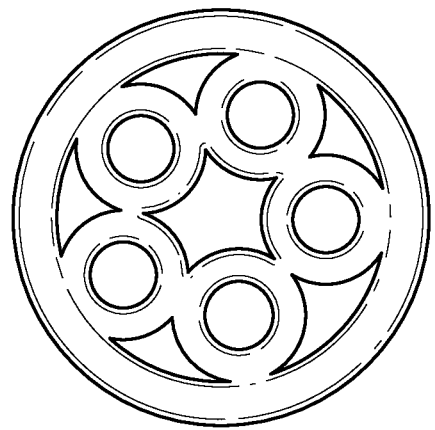
FIG. 17

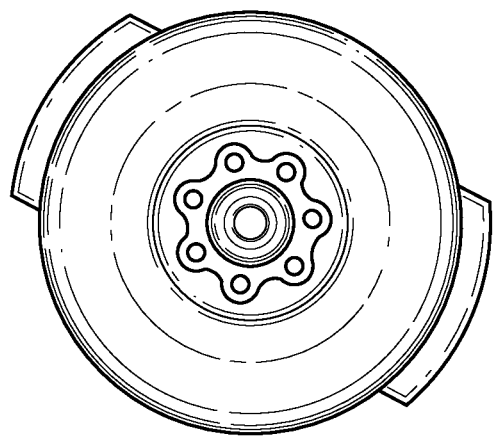
FIG. 19

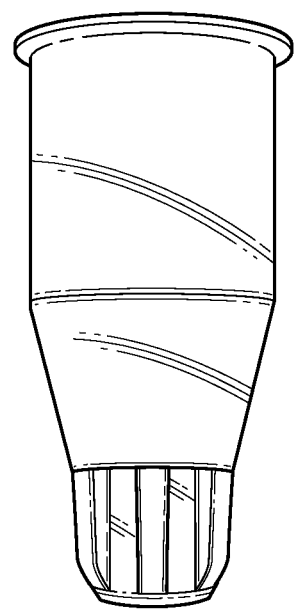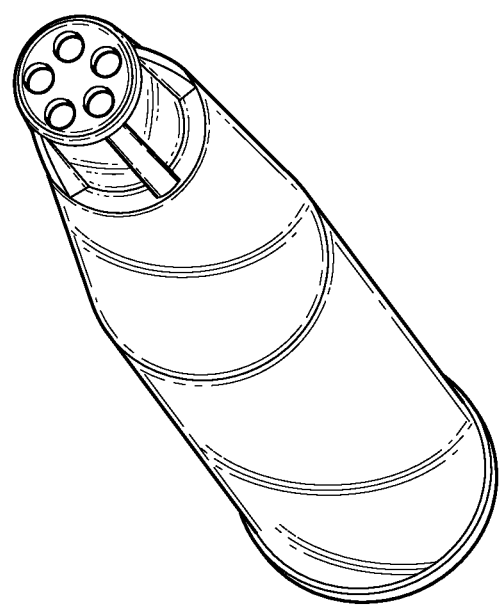
FIG. 20

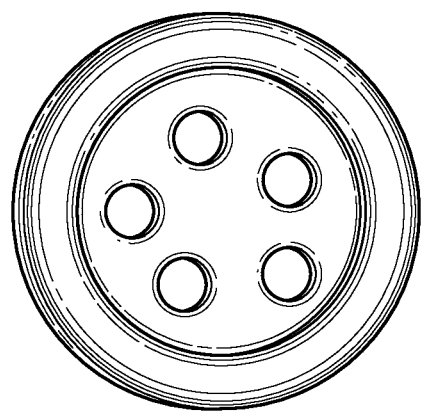
FIG. 21

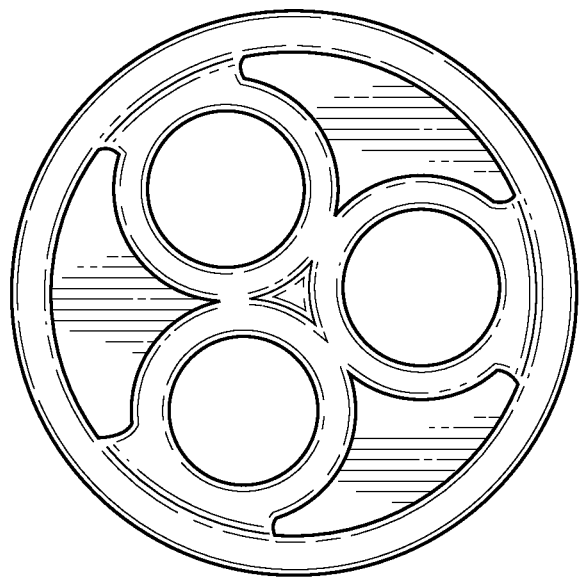
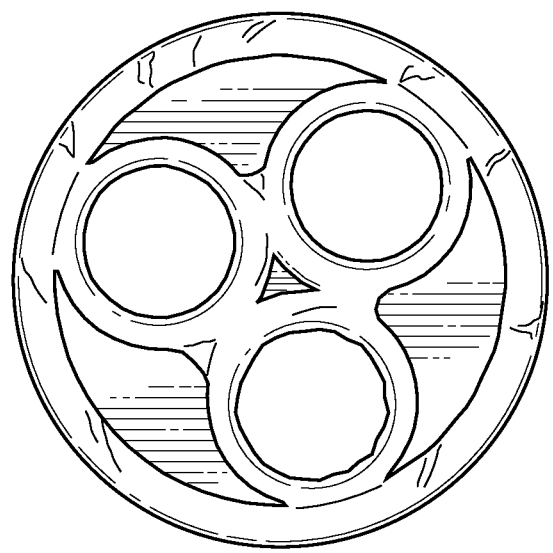
FIG. 23

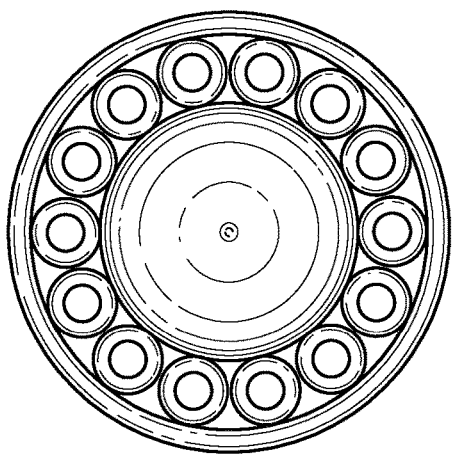
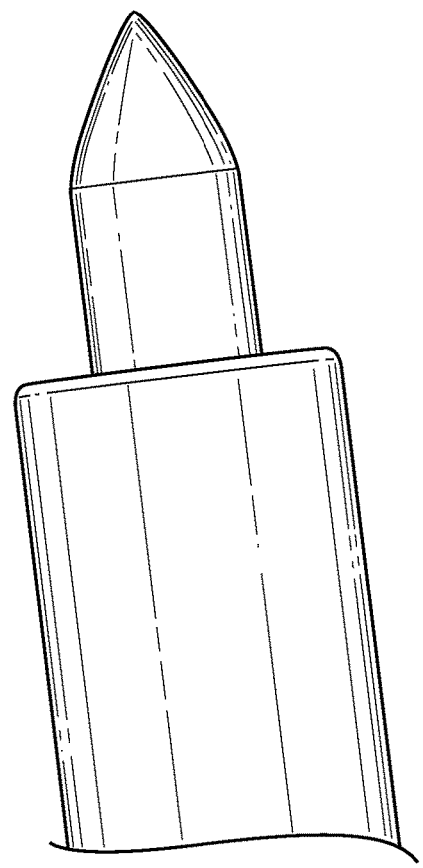
FIG. 24

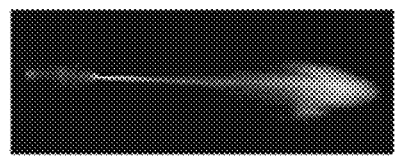
Zero bypass nozzle
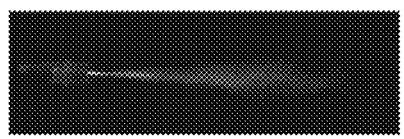
Low bypass nozzle
High bypass nozzle
FIG. 30

NOZZLES FOR NASAL DRUG DELIVERY

CROSS REFERENCE TO RELATED APPLICATIONS

This application is a continuation of an international patent application PCT/US12/37132, filed May 9, 2012, which claims priority from U.S. Provisional Application Ser. No. 61/484,048, filed May 9, 2011, which applications are hereby incorporated by reference herein in their entirety.

STATEMENT CONCERNING GOVERNMENT INTEREST

The instant invention was made with U.S. government funding pursuant to US Army SBIR grant W81XWH-10-C-0238. The Government may have certain rights in this application.

BACKGROUND

Existing nasal drug delivery devices do a poor job of penetrating the nasal cavity to deposit drug onto the medial turbinates for systemic delivery. Such existing devices are also lacking in delivering drug to the upper nasal cavity for direct nose-to-brain delivery. Existing nasal drug delivery devices generate a wide plume which inadequately delivers a compound deep into the nasal cavity.

SUMMARY

In one embodiment, a nozzle is described and claimed including a drug product inlet configured to receive a mixture of aerosolized propellant and an intranasal dosage form, the inlet disposed at the proximal end, a nozzle body defining two or more channels, the channels having a proximal and distal end, the body defining a longitudinal axis, and, an orifice disposed at the distal end of each channel.

In an aspect, the channels are disposed parallel to the longitudinal axis.

In another aspect, the channels are disposed at an angle with respect to the longitudinal axis.

In an aspect, the nozzle includes from five to seven channels.

In an aspect, the channels are circular and tubular in shape.

In an aspect, the channels are conical in shape.

In an aspect, four circular orifice apertures configured in a square orientation are disposed at the distal end of the nozzle.

In an aspect, five circular orifice configured in a pentagonal orientation are disposed at the distal end of the nozzle.

In an aspect, six circular orifice configured in a hexagonal configuration are disposed at the distal end of the nozzle.

In an aspect, six circular orifice configured in a centered pentagonal configuration are disposed at the distal end of the nozzle.

In an aspect, four circular orifice configured linearly are disposed at the distal end of the nozzle.

In an aspect, four rectangular orifice configured radially are disposed at the distal end of the nozzle.

In an aspect, five star-shaped orifice configured in a pentagonal configuration are disposed at the distal end of the nozzle.

In an aspect, the channels are plastic or metal tubes, the body is a plastic or metal tube, and, voids are disposed between the channels and body.

In another embodiment, a nozzle for delivering a compound to an upper olfactory region of a user is disclosed including a nozzle body having a central axis, a plurality of channels housed within the nozzle body, the channels having a proximal end and a distal end, an inlet disposed at the proximal end of the channel, an outlet orifice disposed at the distal end of the channel, the outlet orifice arranged parallel to the central axis of the nozzle.

In an aspect, a line drawn thru a point on the outlet orifice is an equal distance to the central axis of the nozzle.

In an aspect, the outlet orifices are arranged so that a narrow plume exits the nozzle.

In an aspect, the angle of the plume is about 5 degrees, about 4 degrees, about 3 degrees, about 2 degrees, about 1 degree.

In yet another aspect, the angle of the plume is about 5 degrees.

In an aspect, the impact force delivered by the nozzle is decreased.

In an aspect, the delivery time for the compound is decreased.

In another embodiment, a nozzle for delivering a compound to an upper olfactory region of a user is disclosed including a nozzle body, a compound channel housed within the nozzle body, the compound channel having a proximal end and a distal end, the proximal end capable of receiving a compound, the distal end of the compound channel having an outlet orifice, and a propellant channel, the propellant channel having a proximal end and a distal end, the proximal end capable of receiving a propellant, the distal end of the propellant channel having an outlet orifice, the compound channel being centered within the propellant channel wherein the compound and the propellant are capable of being emitted from the from outlet orifice.

In an aspect, the nozzle includes at least a second compound channel, wherein the nozzle is capable of delivering more than one compound at a time.

In another aspect, the compound delivered by the nozzle is a liquid, a powder, a gas, or combinations thereof.

In another aspect, the nozzle further includes a check shut off valve wherein the check shut off valve prevents propellant from flowing through the compound chamber once the compound is released.

DESCRIPTION OF DRAWINGS

FIG. 1 shows cross-sectional side view and distal view of a nozzle embodiment.

FIG. 2 shows a cross-sectional side view of another nozzle embodiment.

FIG. 3 shows a cross-sectional side view of another nozzle embodiment.

FIG. 4 shows a cross-sectional side view of another nozzle embodiment.

FIG. 5 shows a cross-sectional side view of another nozzle embodiment.

FIG. 6 shows a cross-sectional distal view of another nozzle embodiment.

FIG. 7 shows a cross-sectional distal view of another nozzle embodiment.

FIG. 8 shows a cross-sectional distal view of another nozzle embodiment.

FIG. 9 shows a cross-sectional distal view of another nozzle embodiment.

FIG. 10 shows a cross-sectional distal view of another nozzle embodiment.

FIG. 17 is a photograph of the side and distal end of nozzle 18.

FIG. 19 is a photograph of the side and distal end of nozzle 31.

FIG. 20 is a photograph of the side and distal end of nozzle 33.

FIG. 21 is a photograph of the side and distal end of nozzle 17.

FIG. 23 shows nozzle number 4.

FIG. 24 shows nozzle number 7.

Figure 29:
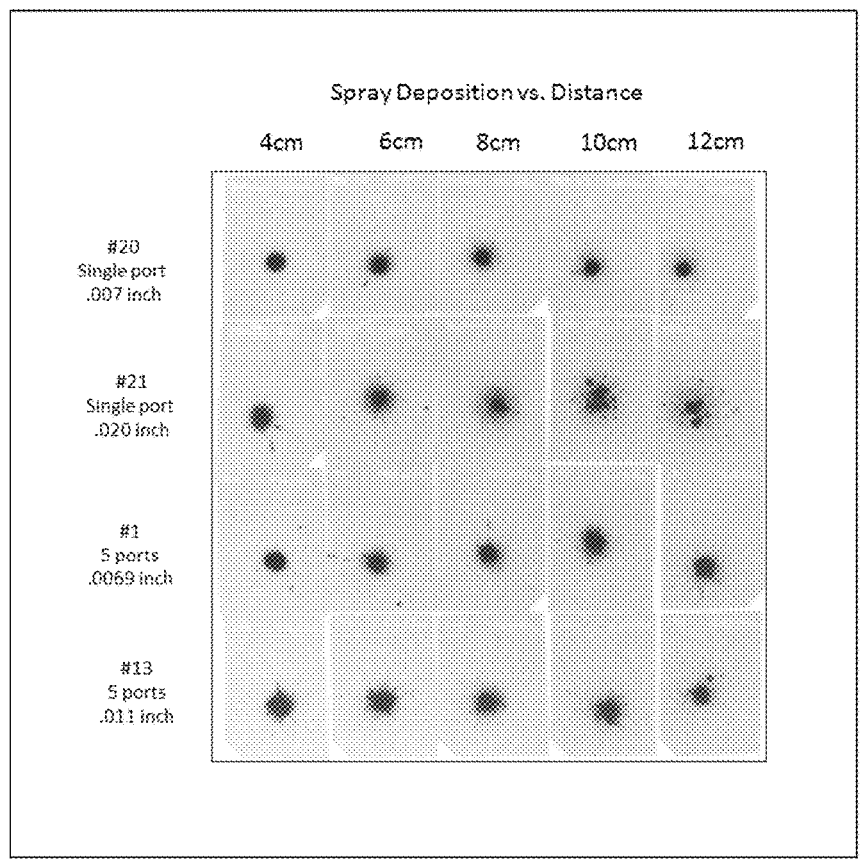

FIG. 29 shows a spray deposition (Method 3) comparison of 4 nozzles, two single channel nozzles and two 5 channel nozzles. Nozzle performance was tested over an extended distance range. To minimize the blotter wicking artifact, dose size was reduced to 10 microliters.

FIG. 30 shows frame captured images from high speed video of powder dosing. Comparison of plume geometry for three powder nozzles.

Figure 31:
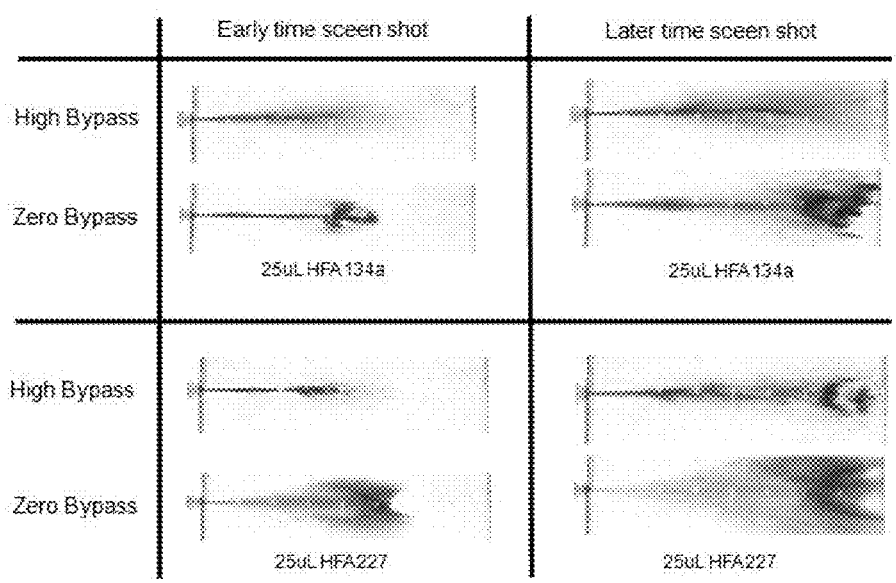

FIG. 31 shows frame capture from high speed video of powder plumes for a zero bypass nozzle (simple tube) and a high bypass nozzle. These shots were carried out between two plastic plates with a spacing of 1.8 mm, dimensions comparable to that found in the nasal sinus. Two times during the development of the plume after actuation initiation are shown. The performances with two different propellants are also compared.

DETAILED DESCRIPTION

Described herein are nozzles that deliver a compound into the posterior regions of the nasal cavity. Current nasal delivery systems do not adequately deposit drug in posterior regions of the nasal cavity such as the respiratory epithelium and olfactory region. Described herein are nozzles that enhance drug deposition into these regions of the nasal cavity.

The nozzles disclosed herein consistently deposit at least a majority fraction of dose into the distal parts of the nasal cavity such as the respiratory epithelium and olfactory region. A drug product (also referred to as drug formulation, intranasal dosage form and other like terms used in the art) is propelled with a velocity via the nozzle into the nasal cavity.

The nozzle may be used to deliver a compound to the upper olfactory region of a mammal or other animal. For instance, the user may be a human or non-human primate. The nozzle may have adult or pediatric users. In some aspects, the nozzle may be used in veterinary medicine. In some aspects, the nozzle may be used to deliver a therapeutic or palliative care compound.

Like named structures in the various embodiments function in the similar or same manner, are structurally the same or similar, and may be used in for the same or similar purpose.

A nozzle is disclosed with a plurality of outlet orifices for delivery of a compound. The nozzle has a central longitudinal axis. The nozzle houses a plurality of channels. The channels have a proximal end at which the compound to be delivered enters the channel and a distal end at which the compound exits the channel via an outlet orifice. In certain embodiments, the channels run parallel to the central axis of the nozzle. In other embodiments, the channels run substantially parallel to the central axis of the nozzle in that a line drawn thru a point on the outlet orifice is of equal distance to the central axis of the nozzle.

The outlet orifices are arranged in parallel alignment with the central axis of the nozzle. In one aspect, the outlet orifices are arranged where a line drawn through the orifice has an equal distance from a line drawn through the center of the nozzle. In yet another aspect, the arrangement of the outlet orifices of the nozzle provides a narrow plume. In yet a further aspect, the outlet orifices are arranged so that the initial path of the compound as it exits the nozzle is substantially parallel to the central axis of the nozzle. In yet another aspect, the outlet orifices are arranged in parallel alignment, in a line of equal distance from a center of the nozzle, in an arrangement that provides for the delivery of a narrow plume, in an arrangement that provides an initial path of the compound as it exits the nozzle substantially parallel to the central axis, or combinations thereof.

In an embodiment, the angle of the plume delivered from the nozzle is about 5 degrees, about 4 degrees, about 3 degrees, about 2 degrees, about 1 degree, inclusive of endpoints. In an embodiment, the angle of the plume delivered from the nozzle is about 5 degrees. In yet another embodiment, the angle of the plume is 5 degrees, is 4 degrees, is 3 degrees, is 2 degrees, or is 1 degree. In a further embodiment, the angle of the plume delivered from the nozzle is 5 degrees.

In embodiments of the nozzle, the impact force delivered by the nozzle having more than one outlet orifice is decreased.

In embodiments of the nozzle, the delivery time is decreased for delivery of a compound by a nozzle having more than one outlet orifice.

In another embodiment of the nozzle, the delivery time and the impact force is decreased by a nozzle having more than one outlet orifice.

In embodiments of the nozzle, the outlet orifices are arranged so that the propellant entrains the compound to be delivered. Without being bound by theory with regards to entrainment of the compound, the multiple streams exiting the nozzle created by the plurality of outlet orifices are better able to entrain air within the plume, thereby shielding the edges of the plume against friction induced turbulence at the edges of the plume.

Figure 1:
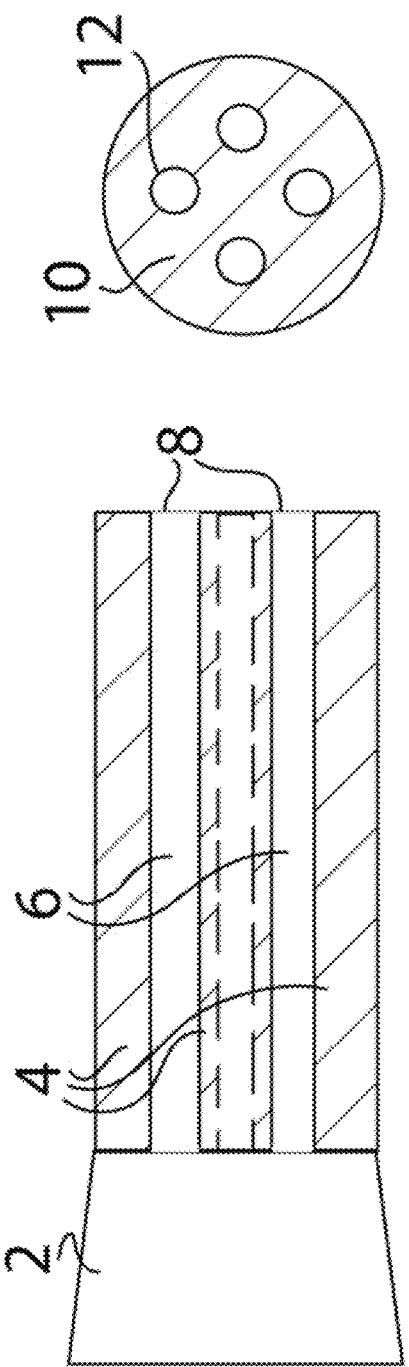

As shown in FIG. 1, a drug product inlet 2 is configured to receive a mixture of gas propellant and a drug formulation. The drug formulation (prior to mixing with the gas propellant) may be in the form of a powder, dispersion, liquid or other suitable nasal delivery dosage form. A nozzle body 4 is secured to the drug product inlet 2. The mixture of gas propellant and drug formulation pass through circular, tube-shaped nozzle channels 6 before exiting the outlet orifices 8, 12 thus releasing the mixture. The circular, tube-shaped nozzle channels 6 aligned parallel to a longitudinal axis running through the center of the nozzle body 4. The distal surface 10 of the nozzle body 4 is shown in the distal view along with the outlet orifices 12.

In one embodiment, the drug product inlet may be optional. In another embodiment, the nozzle has an attachment mechanism to the source of the compound being distributed from the nozzle. The attachment mechanism may be a screw, snap or other suitable mechanism. In another embodiment, the drug product inlet and nozzle may be of uniform construction with the chamber, container or the like holding the compound being delivered. When the drug product inlet is optional, a proximal end of the nozzle functions as the drug product inlet.

The channels may be circular, oval, square, triangular, parallelograms, trapezoidal or combinations thereof.

In one embodiment, the nozzle shown in FIG. 1 is described in Example 6.

Figure 2:
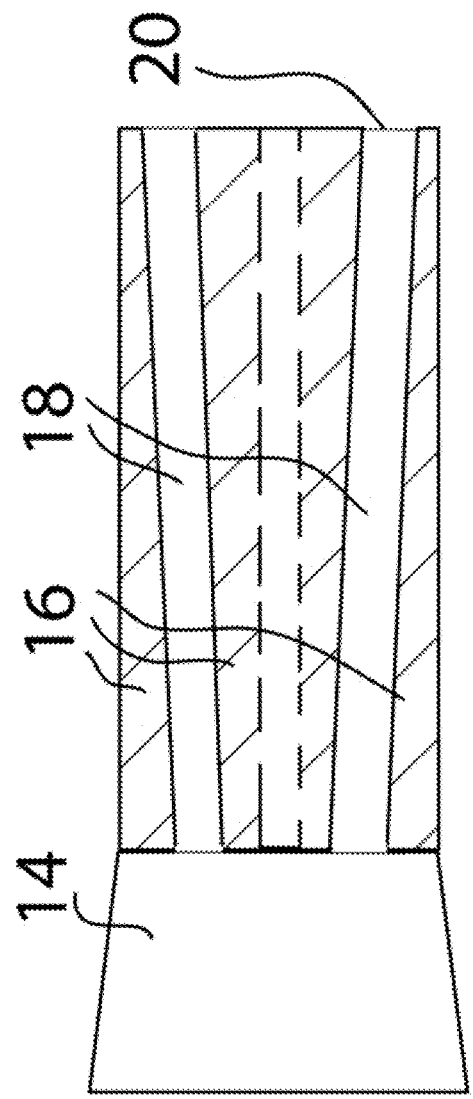

As shown in FIG. 2, a drug product inlet 14 is configured to receive a mixture of gas propellant and a drug formulation. A nozzle body 16 is secured to the drug product inlet 14. The mixture of gas propellant and drug formulation pass through circular, tube-shaped nozzle channels 18 before exiting the outlet orifices 20 thus releasing the mixture. The circular, tube-shaped nozzle channels 18 being tapered away from a longitudinal axis running through the center of the nozzle body 16.

Figure 3:
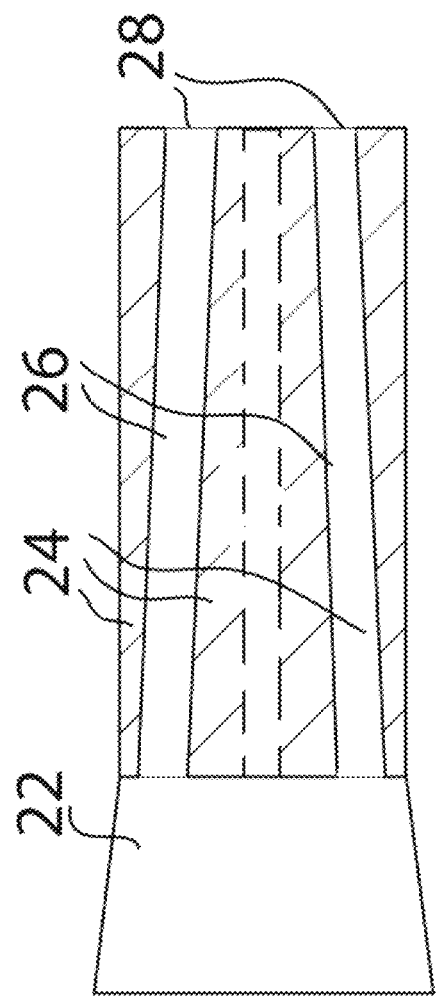

As shown in FIG. 3, a drug product inlet 22 is configured to receive a mixture of gas propellant and a drug formulation. A nozzle body 24 is secured to the drug product inlet 22. The mixture of gas propellant and drug formulation pass through circular, tube-shaped nozzle channels 26 before exiting the outlet orifices 28. The circular, tube-shaped nozzle channels 26 being tapered toward a longitudinal axis running through the center of the nozzle body 24.

Figure 4:
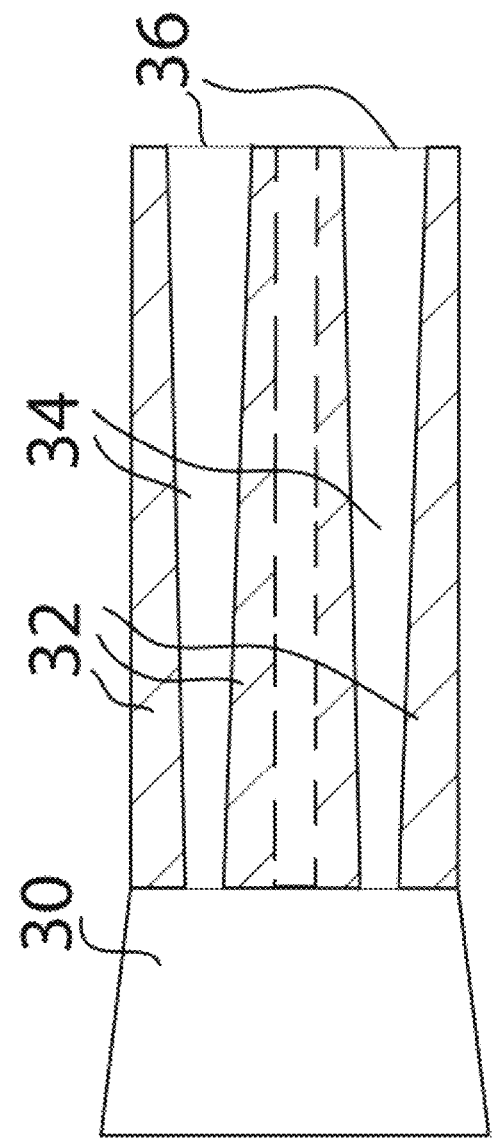

As shown in FIG. 4, a drug product inlet 30 is configured to receive a mixture of gas propellant and drug formulation. A nozzle body 32 is secured to the drug product inlet 30. The mixture of gas propellant and drug formulation pass through conically-shaped channels 34 before exiting the outlet orifices 36 thus releasing the mixture. The conically-shaped channels 34 are aligned to taper away from a longitudinal axis running through the center of the nozzle body 32. The outlet orifices 36 (at the distal end of the channels 34) being larger in diameter than the proximal end of the channels 34.

Figure 5:
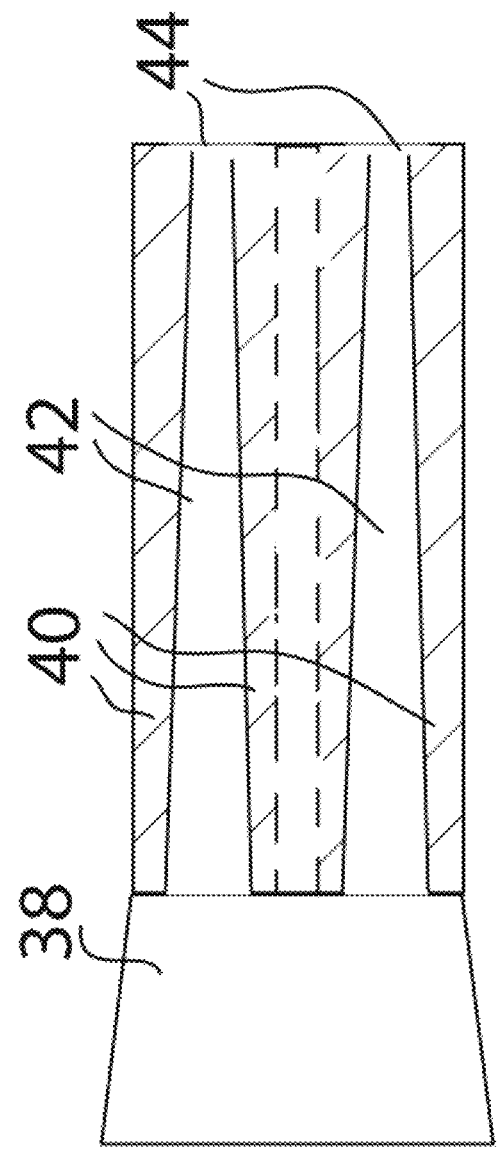

As shown in FIG. 5, a drug product inlet 38 is configured to receive a mixture of gas propellant and drug formulation. A nozzle body 40 is secured to the drug product inlet 38. The mixture of gas propellant and drug formulation pass through conically-shaped channels 42 before exiting the outlet orifices 44 thus releasing the mixture. An axis along the center of the conically-shaped channels 42 being parallel to a longitudinal axis running through the center of the nozzle body 40. The outlet orifices 44 (at the distal end of the channels 42) being smaller in diameter than the channels 42 at the proximal end of the channels 42.

Figure 6:
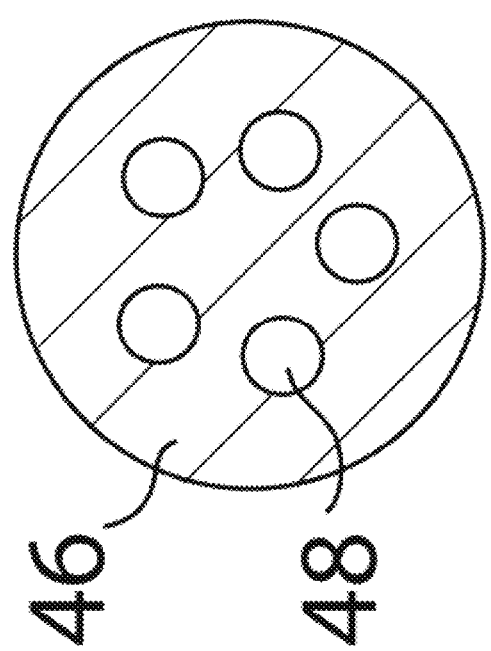
Figure 7:
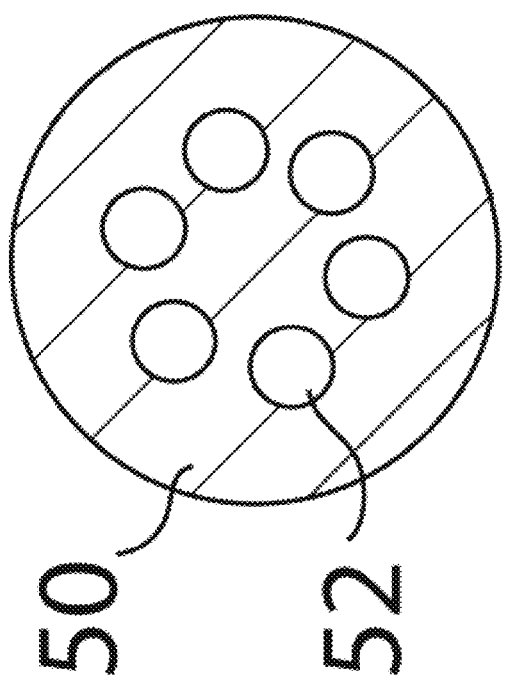
Figure 8:
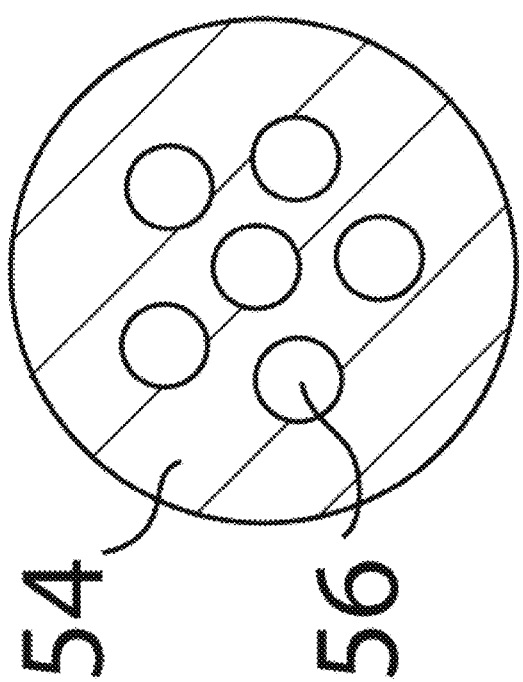
Figure 9:
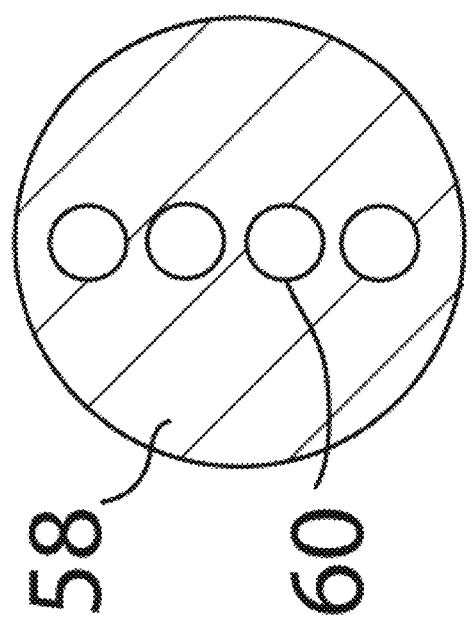
Figure 10:
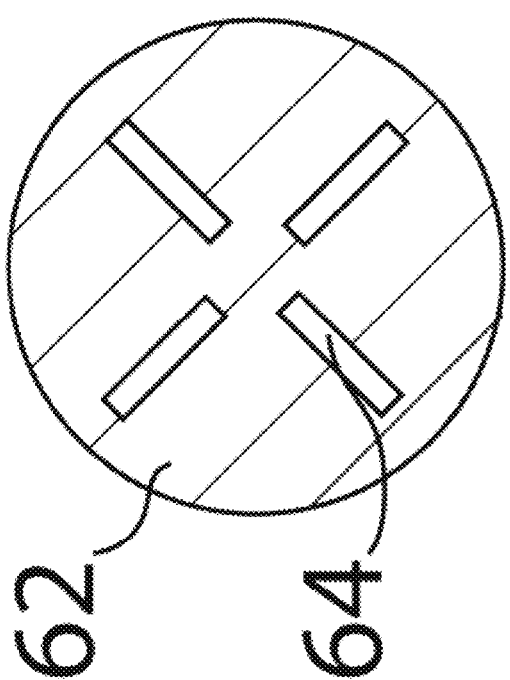
Figure 11:
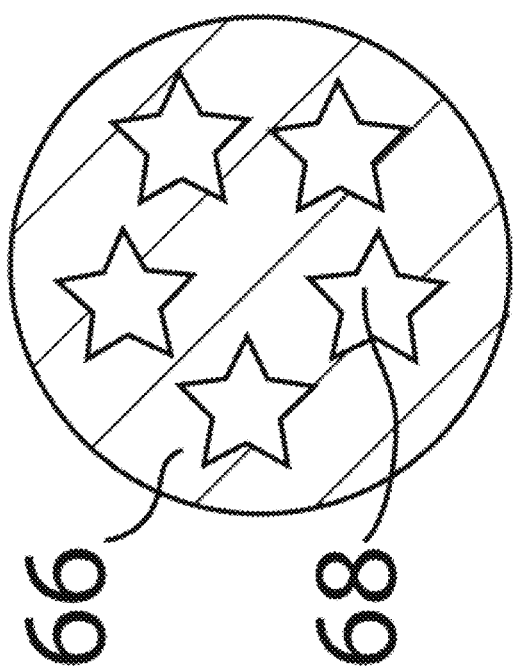
FIG. 11 shows a cross-sectional distal view of another nozzle embodiment.

Shown in FIG. 6 are five (5) circular outlet orifices 48 disposed at the distal end of a nozzle body 46 in a pentagonal orientation. Shown in FIG. 7 are six (6) circular outlet orifices 52 disposed at the distal end of a nozzle body 50 in a hexagonal orientation. Shown in FIG. 8 are six (6) circular outlet orifices 56 disposed at the distal end of a nozzle body 54 in a centered-pentagonal orientation. Shown in FIG. 9 are four (4) circular outlet orifices 60 disposed at the distal end of a nozzle body 58 in a linear orientation. Shown in FIG. 10 are four (4) rectangular outlet orifices 64 disposed at the distal end of a nozzle body 62 in a radial orientation. Shown in FIG. 11 are five (5) star-shaped outlet orifices 68 disposed at the distal end of a nozzle body 66 in a pentagonal orientation. As shown in FIGS. 6-11, the volume between outlet orifices 48, 52, 56, 60, 64, 68 is solid. In another embodiment, the volumes may be void, partially void or partially solid.

In one embodiment, the outlet orifices are square, circular, oval, trapezoidal, parallelograms, triangular, star shaped, or combinations thereof.

In one embodiment, the nozzle shown in FIG. 6 is described in Example 1.

In another embodiment, the nozzle shown in FIG. 9 is described in Example 3.

Figure 12:
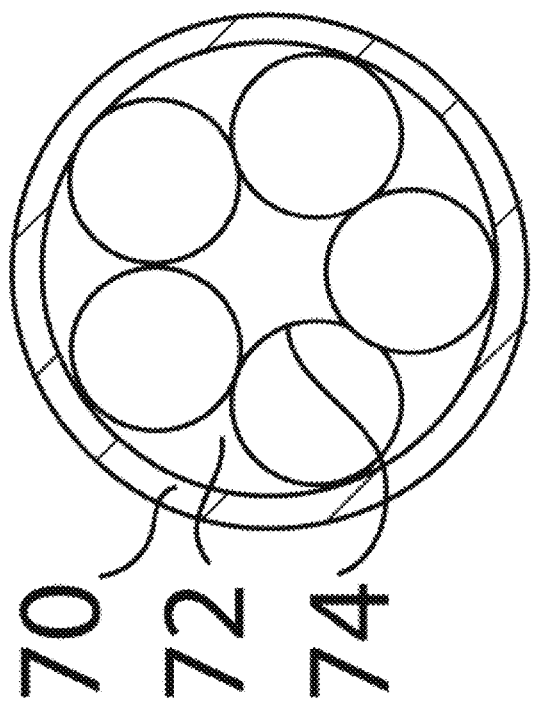
FIG. 12 shows a cross-sectional distal view of another nozzle embodiment.

Shown in FIG. 12 are five (5) circular outlet orifices 74 disposed at the distal end of the nozzle body 70 in a pentagonal orientation. In this embodiment, the volume 72 between the channels is void (e.g., an air gap).

In one embodiment, the nozzle shown in FIG. 12 is described in Example 2.

Figure 13:
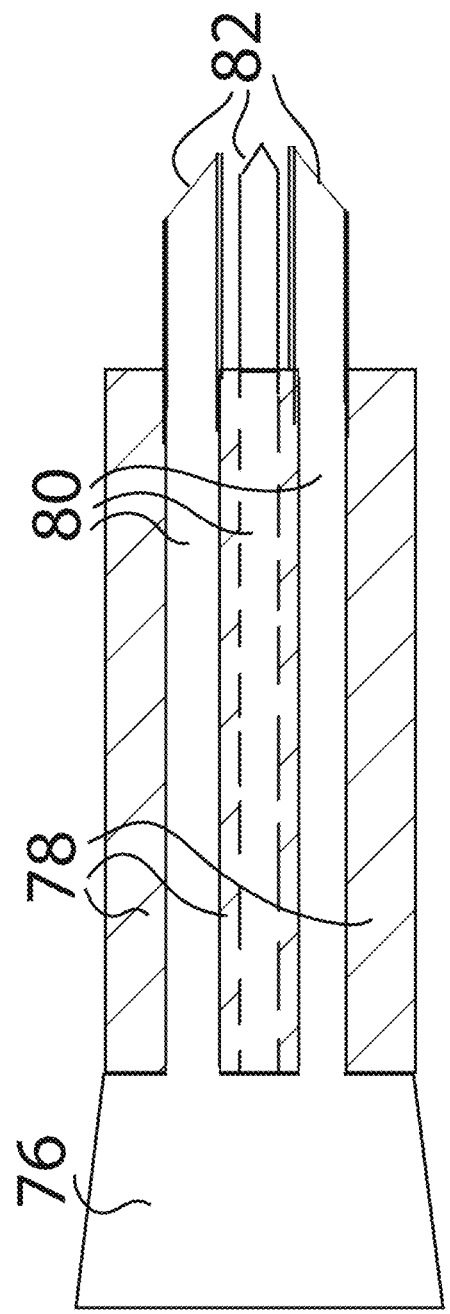
FIG. 13 shows a cross-sectional side view of another nozzle embodiment.
Figure 18:
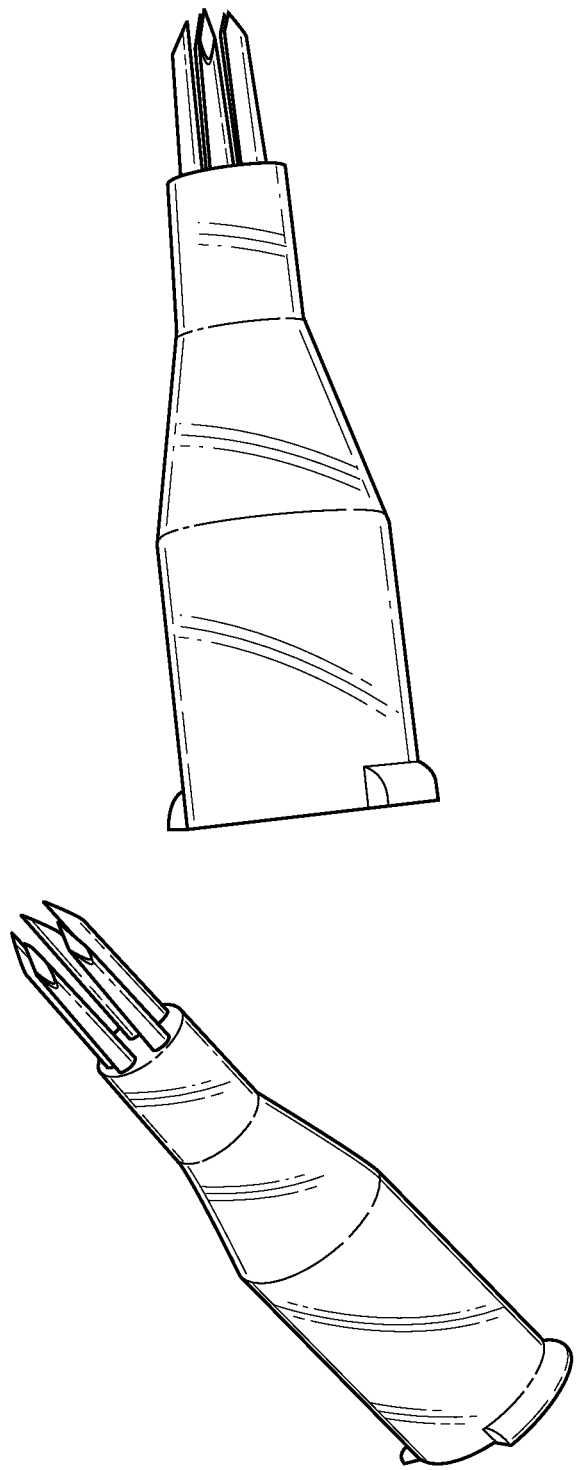
FIG. 18 is a photograph of the side and distal end of nozzle 35B.
Figure 22:
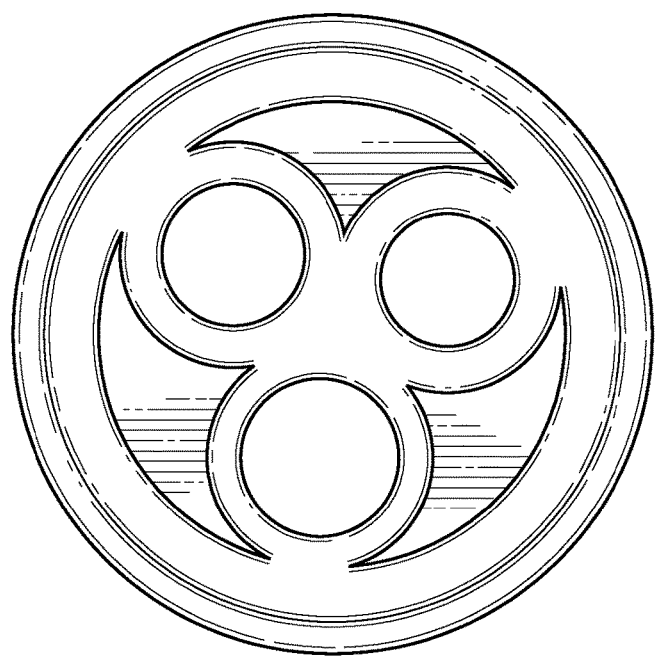
FIG. 22 shows nozzle number 3.

As shown in FIG. 13, a drug product inlet 76 is configured to receive a mixture of gas propellant and a drug formulation. A nozzle body 78 is secured to the drug product inlet 76. The mixture of gas propellant and drug formulation pass through circular, tube-shaped nozzle channels 80 before exiting the outlet orifices 82 thus releasing the mixture. In this embodiment the outlet orifices channels 80 extend beyond the nozzle body 78 and terminate at the outlet orifices 82 which are biased with the biased edge oriented near to and parallel to a longitudinal axis running through the center of the nozzle body 78. Nozzle #35B, as shown in FIG. 18, has outlet orifice channels which extend beyond the nozzle body.

In one embodiment, the nozzle shown in FIG. 13 is described in Example 4.

Figure 14:
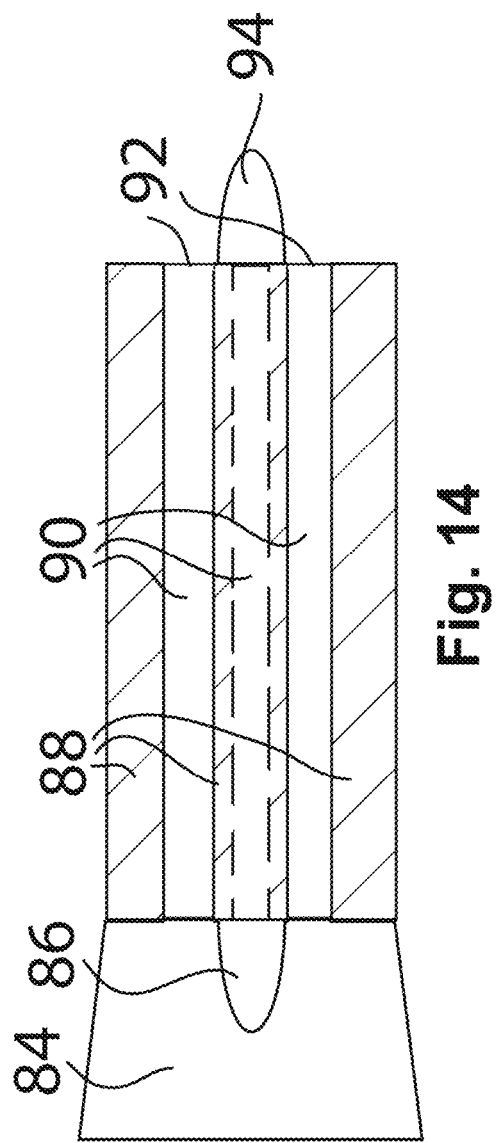
FIG. 14 shows a cross-sectional side view of another nozzle embodiment.
Figure 15:
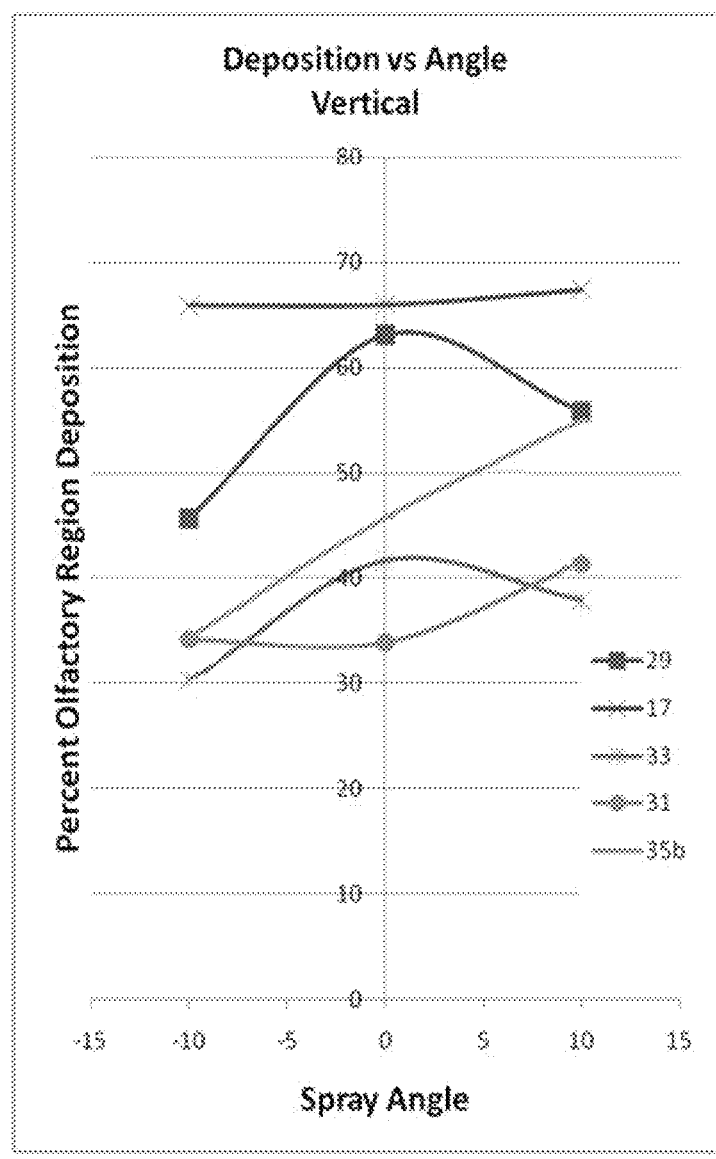
FIG. 15 is a graph of percent deposition versus vertical spray angle for various nozzle and outlet orifice embodiments set forth in the Examples and Figures herein. In this graph the zero angle is defined as the optimal angle from the naris to the olfactory region.
Figure 16:
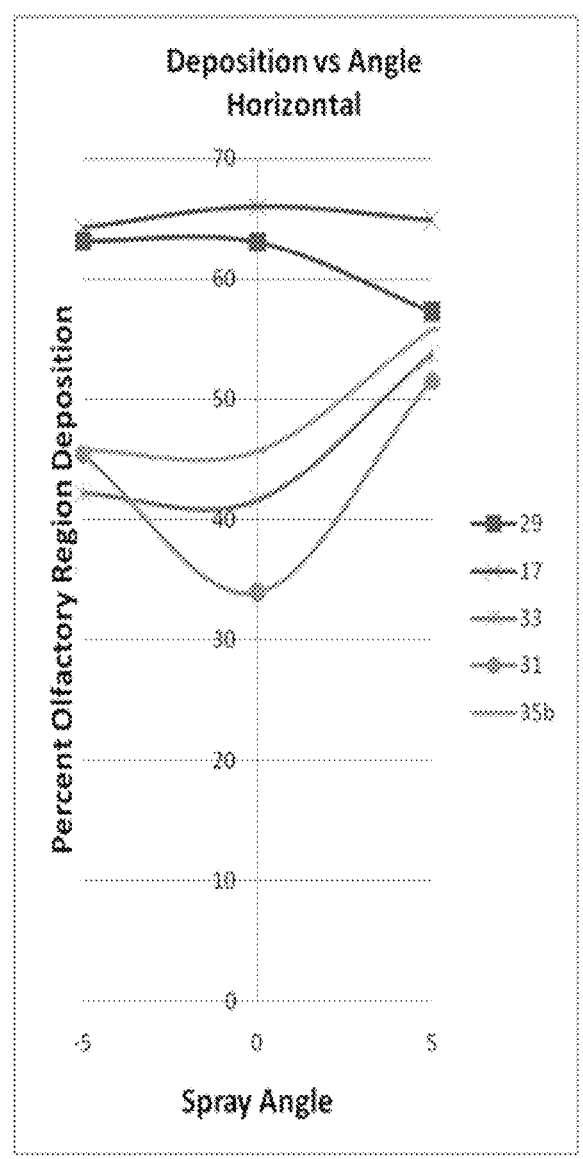
FIG. 16 is a graph of percent deposition versus horizontal spray angle for various nozzle and outlet orifice embodiments set forth in the Examples and Figures herein. In this graph the zero angle is defined as the optimal angle from the naris to the olfactory region.

As shown in FIG. 14, a drug product inlet 84 is configured to receive a mixture of gas propellant and a drug formulation. A nozzle body 88 is secured to the drug product inlet 84. The mixture of gas propellant and drug formulation pass through circular, tube-shaped nozzle channels 90 before exiting the outlet orifices 92 thus releasing the mixture. In this embodiment there is a rounded inlet guide 86 attached to the nozzle body 88 and pointed into the drug product inlet 84 which directs the drug product into the nozzle channels 90. There also exists an outlet directional guide which guides the drug product coming out of the outlet orifices 92 to help maintain a narrow drug product spray. The nozzle is nozzle 31 shown in FIG. 19.

In one embodiment, the nozzle shown in FIG. 19 is described in Example 5.

Figure 27:
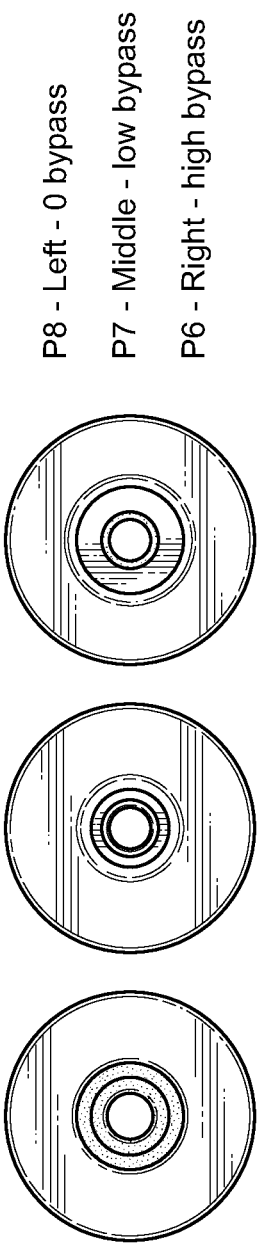
FIG. 27 shows nozzles A, B, and C of Example 11.
Figure 28:
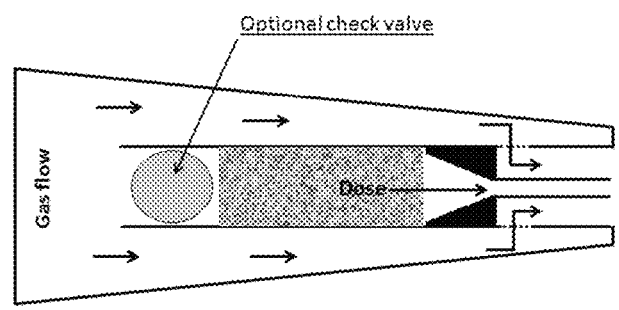
FIG. 28 shows nozzle D of Example 11.

As shown in FIGS. 27 and 28, a bypass nozzle is shown and described. Nozzle C (Example 11) describes an annular gas bypass nozzle. Nozzle C includes a chamber for the compound to be delivered and a chamber for the propellant. In one aspect, the compound is a drug and the propellant is a gas. The drug may be in liquid or powder form. Nozzle C includes a channel to transport the drug. This drug channel is centered inside of another channel, the propellant channel, which serves to deliver the propellant. In one aspect, the drug channel transports a powder while the propellant channel delivers a gas. The dimensions of the drug channel with respect to the propellant channel affects the amount and velocity of gas emitted from the outlet of the nozzle. Both the powder transport channel and the gas channel can be altered to change the performance of the nozzle assembly, as discussed in Example 11.

Upon actuation of nozzle C, both chambers are pressurized and gas is emitted from the end of the nozzle as a uniform and symmetrical hollow cylinder, while at the same time the dose is emitted into the center of the gas cylinder. Depending on the configuration of the two channels and the amount and type of gas used to drive the nozzle, the relative velocity of the gas and powder streams can be different, causing different effects on performance. In one embodiment, multiple dose transport channels are placed in the center of the gas transport tube so that this nozzle design would deliver doses of more than one drug at the same time with minimal mixing before the drugs are deposited on the target surface or tissue.

In one embodiment, the drug channel can transport a liquid, a powder, a gas, or combinations thereof.

In one embodiment, a bypass nozzle D is shown as in FIG. 28. Nozzle D shows a check shut off valve. The valve includes a ball of plastic slightly smaller than the diameter of the compound chamber behind the nozzle. Upon activation of the device, the ball rolls up behind the drug and seats on the back side of nozzle D, thereby effectively preventing gas flow through the drug channel once the drug is released.

A variety of compounds may be delivered by the nozzle. In one embodiment, a mixture of drug and gas propellant is delivered by the nozzle. In another embodiment, a mixture of liquid propellant and drug is delivered by the nozzle. In another embodiment, a liquid propellant is delivered by the nozzle. In yet another embodiment, a drug is delivered by the nozzle. In yet other embodiments, a combination of compounds is delivered by the nozzle.

The compound delivered by the nozzle may be a liquid, gas, solid, or combinations thereof. The compound may be a liquid or a powder. The compound may be a drug.

The nozzle may be used to deliver compounds to many environments. The nozzle may be used to deliver a compound intranasally. The nozzle may be used to deliver a compound orally, rectally, vaginally, topically, to the eye, or intranasally.

The nozzle may be used to deliver medicaments or other compounds not for therapeutic use. For example, the nozzle may be used to deliver a precise plume in manufacturing.

EXAMPLES

Set forth below are examples of nozzles and outlet orifices.

Example 1

In nozzle number 1, a five outlet nozzle was constructed of 30 gauge (G) stainless steel tubes, (approximately 0.0069 inch circular orifice and approximately 5 mm in length) mounted within a 20G stainless steel tube. The 30G tubes fit tightly and formed a symmetric pentagonal arrangement that would lie symmetrically on a circle. All non-orifice gaps between the individual 30G tubes were filled. The distal end of the nozzle was finished with all tubes flush and of equal length. The openings were finished clean and square.

Example 2

Nozzle number 2 was constructed having 11 outlets composed of 5, 25G stainless tubes (approximately 0.011 inch circular orifice and approximately 5 mm in length) mounted within an 18G stainless steel tube for a tight fit. No voids between the 25G and 15G tubes were filled, so the nozzle configuration had 5 additional ports, approximately triangular in shape, the nozzle ports surrounding the 5 circular ports. In addition, a central void of roughly pentagonal shape exists at the very center which was capable of passing a dose. The distal end of the nozzle was finished with all tubes flush and of equal length. The openings were finished clean and square.

Nozzle number 3, as shown in FIG. 22, was constructed having 6 outlets composed of 3, 23G stainless tubes assembled into a 15G stainless steel tube. These fit tightly and no glue or filler was used. In addition to the three nozzle ports from the 23G tubes, there were three additional approximately triangular shaped outlets from the nozzle. The distal end of the nozzle was finished with all tubes flush and of equal length. The openings were finished clean and square.

Nozzle number 10 has some of the same components used to assemble nozzle number 3. For nozzle number 10, each 23G stainless tube has an approximately 30 degree bend in the last 2 mm of the tube at the distal end of the nozzle. These tubes were inserted into a 14G stainless steel tube so that their orientation was all the same around the perimeter of the 14G tube. These were held in place with a central brass rod. The distal end of the nozzle was finished with all tubes flush and of equal length. The openings were finished clean and square. Because of the 30 degree bend in the 23G tubes, they are oval in dimensions and not round. All voids between elements were open.

Nozzle number 11 has some of the same components of nozzle number 9 (Example 3) with straight 23G stainless steel tubes set into a 14G stainless steel tube. No brass rod was used to hold the tubes in, with the 14G tube being lightly crimped. The distal end of the nozzle was finished with all tubes flush and of equal length. The openings were finished clean and square. All voids between elements were open.

Nozzle number 13 has some of the same components as nozzle number 2. Similar to nozzle number 1 (Example 1), nozzle number 13 has all intervening open voids filled leaving 5 active nozzle ports in the same special relationship as those in nozzle number 2.

Example 3

Nozzle number 5 has four outlets of 30G stainless steel tubes in a linear arrangement within a modified 16G stainless steel tube. The 30G tubes were set by light crimping of the 16G tube and filler was applied to fill all voids between the 30G and 16G tubes. The distal end of the nozzle was finished with all tubes flush and of equal length. The openings were finished clean and square.

Example 4

Nozzle number 12 has five outlets consisting of 27G stainless steel needle ends arranged with the pointed ends extending beyond the end of the nozzle housing (a 16G stainless steel tube). All five 27G needles were arranged so that the point was placed closest to the center of the assembly. The assembly of 5 needles was secured within the 16G tube under tension from a centrally placed brass rod. The brass rod was tapered so that a tension fit held everything together. All voids other than the 5 outlet ports were filled with epoxy prior to final assembly. The resulting nozzle had a tapered distal end that extended approximately 2.66 mm from the end of the 16G nozzle housing. All port surfaces were finished clean and square.

Nozzle 19 is a composite assembly of nozzle number 37 (Example 6) with 27G stainless steel needles inserted into the port channels of a nozzle number 37 nozzle assembly. The needles extend from the plastic end of the distal end of the nozzle by approximately 5.5 mm. The needles are all arranged so that the tip side of each needle is oriented toward the center of the nozzle. They lie closest to the central axis of the nozzle.

Example 5

Nozzle number 14 has seven outlet ports arranged around a central aerodynamic extension, analogous to nozzle number 7 (Example 8 and FIG. 24). Nozzle number 14 was cast in plastic rather than assembled with stainless steel tubing. The central extension is 2.15 mm in diameter at the point that it joins the distal end of the nozzle and tapers in an aerodynamic fashion. The port channels are straight and parallel to the nozzle axis. The port channels are 5.5 mm long. The nozzle assembly includes a female luer lock.

Nozzle number 15 is similar to nozzle number 14 but with the body of the section of the assembly before the nozzle proper being shorter while still including a female luer lock. Nozzle number 15 is cast entirely in plastic as a unit.

Example 6

Nozzle number 16 has 4 outlet ports arranged approximately 0.7 mm apart and equidistant in a square pattern. Nozzle number 16 has a similar female luer lock design as for nozzle number 15 (Example 5). Port lumen lengths are approximately 5.3 mm in length, parallel to each other and on axis with the nozzle body. Cast entirely in plastic as a unit.

Nozzle number 37 is similar to nozzle number 16, except 5 outlet ports arranged equidistant to each other and as if placed on a circle or the apices of a pentagon. Port channel lengths are 5.3 mm and include the same luer lock as nozzle number 16. Cast entirely in plastic as a unit.

Nozzle number 38 has 4 outlet ports as in nozzle number 16. The port channels of nozzle number 38 traverse 10.3 mm and they possess a right handed twist (as viewed at the distal end) of approximately 180 degrees in that distance. The nozzle is longer than nozzle 16 and contains the same luer features and spatial details as nozzle 16. Cast entirely in plastic as a unit.

Example 7

Nozzle number 4, as shown in FIG. 23, was constructed having 7 outlets composed of 3, 25G stainless tubes (approximately 21 mm in length) assembled into a 15G stainless tube. The 15G tube was lightly crimped on its perimeter to secure the 25G tubes within the body. No adhesive was used and all voids remained open. The distal end of the nozzle was finished with all tubes flush and of equal length. The openings were finished clean and square.

Example 8

Nozzle number 7, as shown in FIG. 24, was constructed of 14, 30G stainless steel tubes arranged within a 14G stainless tube around a central steel aerodynamically sculpted pin. The 30G tubes are 14 mm in length and are seated flush with the end of the 14G nozzle housing. The central pin is approximately 1.12 mm in diameter. It protrudes from the distal end of the nozzle by 2.38 mm. No glue is used to set these elements within the 14G tube. All perimeter voids participate in the movement of liquid and gas through the nozzle. Except for the extended central pin, the distal end of the nozzle was finished with all tubes flush and of equal length. The openings were finished clean and square.

Example 9

Figure 25:
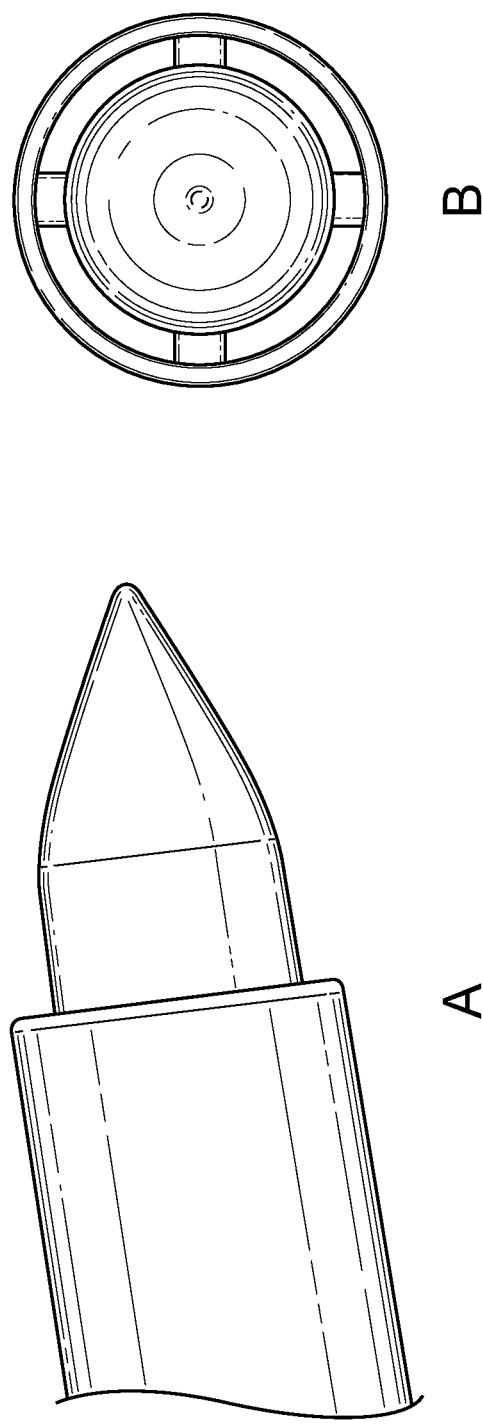
FIG. 25 shows nozzle number 8.

Nozzle number 8, as shown in FIG. 25, has similarities to nozzle number 7 described in Example 8 without the use of 30G tubes on the periphery. Thin rectangular brass standoffs were used to center the central pin within the 14G stainless steel tube. Eight standoffs were required to center and maintain the pin in a linear orientation with respect to the 14G tube.

Example 10

Figure 26:
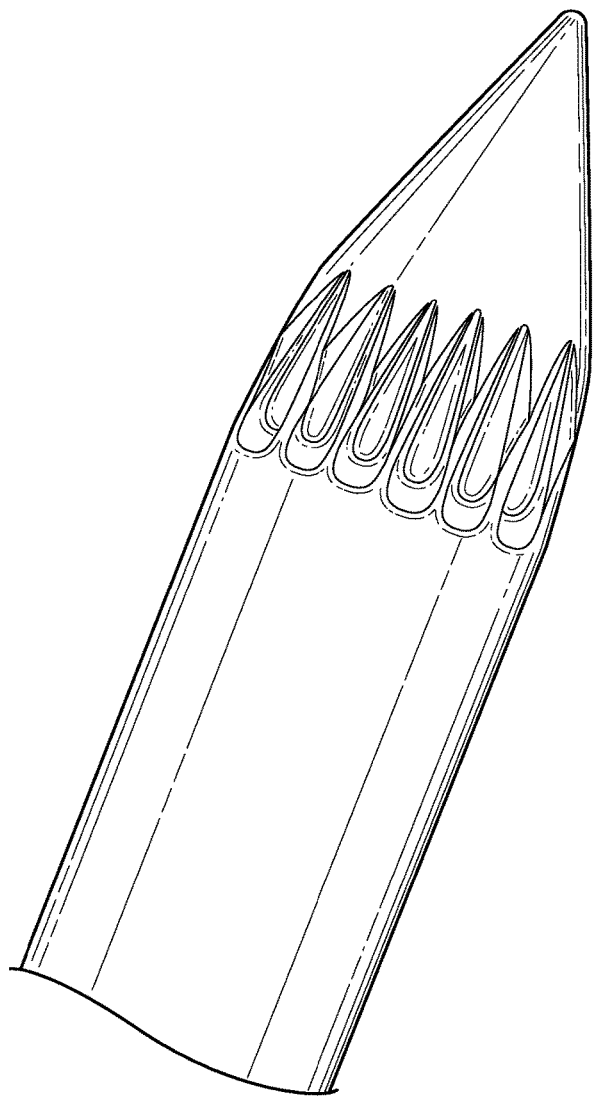
FIG. 26 shows nozzle number 9.

Nozzle number 9, as shown in FIG. 26, is constructed of 14, 30G stainless steel needle tips with similarities to the 30G tubes of nozzle number 7. These tubes are mounted around the same type of central steel aerodynamically sculpted pin. Each tapered needle tip is mounted with the long side placed against the steel pin. The result is a 3 mm tapered extension at the distal end beyond the edge of the 14G nozzle housing.

Example 11

Nozzles for the delivery of a dry powdered dose.

The nozzles of this Example are shown in FIGS. 27 and 28.

Nozzle A. Single port nozzle. Several configurations of solid plastic drilled with a straight exit port of varying lengths were tested. A 4.45 mm diameter plastic nozzle with a single 1.07 mm internal diameter port of approximately 1 cm in length was tested. Also tested was a 4.45 mm in diameter nozzle with a single 0.67 mm internal diameter port of 8.75 mm in length. A third configuration was a nozzle of approximately 1 cm in length with a single nozzle port of 0.031 inch internal diameter. The powder is driven through the port tube by gas pressure.

Nozzle B. Multiple port nozzle. Drilled in PEEK plastic. 5 nozzle ports of internal diameter of 0.015 inch. Orifice diameters are 0.011 inches. The dose is driven through the multiple ports by gas pressure.

Nozzle C. Single port annular gas bypass nozzle. Two configurations were designed and tested. This nozzle design is a two compartment nozzle, one for the dose and one for gas. These nozzles feature a straight 0.031 in internal diameter port tube that transports the powder. This transport tube is centered inside of another tube that serves to deliver a stream of gas. The configurations tested have different gas tube diameters and therefore affect the amount and velocity of gas emitted from the end of the nozzle. Both the powder transport tube and the gas tubes can be altered to change the performance of the nozzle assembly. These test configurations were designed to be driven by a single source of compressed gas (e.g. hydrofluoroalkane), but each compartment of the nozzle could be independently driven. Upon actuation, both chambers are pressurized and gas is emitted from the end of the nozzle as a uniform and symmetrical hollow cylinder, while at the same time the dose is emitted into the center of the gas cylinder. Depending on the configuration of the two tubes and the amount and type of gas used to drive the nozzle, the relative velocity of the gas and powder streams can be different, causing different effects on performance.

The inner diameter of the dose tube is 0.031 in for all three nozzles. The zero (0) bypass nozzle is the third configuration described in A above. Low bypass nozzle has a gas tube gap of 0.008 in. The high bypass nozzle has a gas tube gap of 0.016 in.

Nozzle D. A variant of nozzle C was made and tested, shown in FIG. 28. It is possible that excess propellant gas emitted from the dose tube after the dose chamber is emptied of powder can cause interference with the plume. In that event, a check shutoff valve was conceived and tested. The valve consisted of a ball of plastic slightly smaller than the diameter of the dose chamber behind the nozzle. Upon activation of the device, the ball rolls up behind the dose and then seats on the back side of the nozzle, thereby effectively preventing gas flow through the dose tube once the dose is gone.

Example 12

Analytical Methods Employed for Nozzle Testing
Plume Geometry

Plume angle was tested as a performance criterion. The testing of the nozzles included establishing the angle of the plume and/or the size of the deposition area at a fixed distance from the nozzle tip.

1) Photography. The pattern of expelled high pressure water from the nozzle was photographed and the angle described by the pattern on the printed photo was measured. This method proved to be accurate and reproducible. Additional methods would look at describing the plume angle of an aerosolized plume as would be generated during actual use. Photography data was used as comparison data for the nozzles described herein.

2) Blotter paper deposition. A method was developed that relied on the deposition of a stained (Fluorescein) aqueous dose emitted from a nozzle onto a blotter paper held at a distance of 4 cm. 4 cm was chosen as a distance relevant to the distance needed to traverse from a likely nozzle tip position in the human naris to the upper olfactory region of the human nasal sinus. This blotter paper deposition assay offered the advantage of creating a permanent record of the dose deposition. In addition, it would be capable of showing any asymmetry in plume geometry. Plume angles were calculated using the blotter paper deposition. A limitation of this method is that the dose staining can bleed beyond the region of deposition, thereby making the observed deposition spot to be larger than the actual deposition zone. This is especially true for larger dose volumes and for nozzles that concentrate the dose into the smallest zone. Another limitation is that the method describes the end result of the deposition and cannot describe how deposition occurs over the course of the event. This limitation yields less information about the nature of the plume as it starts, progresses and ends. It can say very little about how the plume is affected by its travels through the air from nozzle to target.

Two additional approaches designed to analyze plume geometry during the time course of dose delivery were applied.

3) High speed blotter recording, with dose deposition onto a rapidly spinning blotter paper target. This method is able to create a physical record of deposition over time. The blotter disk can be rotated fast enough so that dose spread is reduced and appears to yield accurate plume geometries displayed during the full shot. It appears to be able to discriminate between different nozzle designs and can catch asymmetries in plume geometry.

4) The second method is high speed videography (greater than 200 frames per second) enhanced with fluorescent dye and lighting. This method appears capable of discriminating the performance between different nozzle designs and can record defects in performance. This method has been adapted for studying nozzle performance under various situations, such as free air performance and within human nasal models.

5) An adaptation of method high speed videography. Modified lighting conditions were used to enhance the visualization of powder doses. In some cases lighting was adjusted so that only limited sections of the spray plume were visible. White light illumination is valuable for seeing the overall plume geometry for powder, however white light is easily scattered and is not able to report on the various dose densities within a plume and likely best highlights the surface of a powder plume. Using single wavelength light in the red spectrum is able to reduce light scatter and better penetrate a powder plume.

Dose Deposition

Previous methods are principally directed at understanding plume geometry generated by each nozzle. We used these methods to attain certain pre-determined performance parameters, such as symmetrical and narrow plumes, to predict actual performance in use. An in vitro method for assessing nozzle performance was to measure dose deposition efficiency in human nasal models. We have employed several methods for this, differing mostly in the manner in which we quantitate the amount of dose deposited in different areas of the human nasal sinus. Of the three methods developed, here we report data generated from two methods.

5) One method assessed deposition by dose weight and was able to report only dose weight deposited in our upper olfactory region of interest (ROI) and elsewhere.

6) Another method reports dose deposition through optical densitometry. This method is capable of reporting fractional deposition within our upper olfactory ROI as well as any number of other ROI that are user defined.

Impact Force

Another physical performance characteristic that affected nozzle design was the impact force generated by the developed plume from any nozzle. We developed a method that records impact force profiles (including maximal impact force) for the duration of a dose shot. Forces generated during dosing could be compared to other commercially available nasal spray devices.

Results:

Plume Geometry:

Many of the nozzles described herein have principle deposition zone dimensions of 3 mm or less when fired 4 cm from the target with relatively minor amounts of dose outside of 5 mm. This represents a plume angle of about 5 degrees or under. It should be noted that the dimensions of the upper olfactory region of the human nasal sinus is on the order of several mm eventually narrowing down to 1-2 mm.

An early deposition study (method 5) along with a study with method 3 allowed a direct comparison between some of the nozzles described in this application with a nozzle designed to generate a rotating plume and also to a single port device (urethral tip).

TABLE 1

| Nozzle Name | Deposition Zone Dimensions - Method #3 | % Olfactory Deposition - Method 5 Direct aim | 10 degrees posterior | 10 degrees anterior | 5 degrees toward septum | 5 degrees away from septum |
|---|---|---|---|---|---|---|
| Rotational Plume Prototype | 25-30 mm | 2.8 | 4.2 | 9.9 | 1.23 | 2.4 |
| #18 | 25 mm | 19 | 12.5 | 20.9 | 22 | 16 |
| #2 | 13 mm | 58.3 | 30.2 | 49.1 | 45.6 | 54.8 |
| #13 | 8 mm | 59.4 | 45.7 | 55.9 | 63.2 | 57.3 |
| #1 | * | 66 | 66 | 67.4 | 64.3 | 65 |
| Urethral Tip | ** | 56.5 | 28.7 | 39.5 | 35.8 | 52.3 |

* Not done concurrently with the other nozzles under the same conditions, however, later comparisons between #1 and #13 reveal that #1 has a smaller deposit footprint than #13.
 Not done As shown in Table 1, high speed blotter paper deposition analysis was carried out with each nozzle in this experiment with the exceptions of nozzle number 1 and the urethral tip. Later comparisons with nozzle number 1 revealed that nozzle number 1 is able to achieve the smallest deposition zone for any of the nozzles tested. The urethral tip is also able to achieve a deposition zone approaching that of nozzle number 13**.

The deposition study presented in Table 1 shows the average from at least three nozzle firings for each nozzle and each aim angle. All conditions of firing were the same for all the nozzles and for each firing condition studied. A correlation can be made between the size of the dose deposition zone and the percent of dose deposited in the upper olfactory region of a human nasal model. The correlation persists regardless of the aim angle used for these shots. We conclude that the smaller the dose plume angle is, the higher the deposition in our ROI. Not expected from these results is that some of the nozzles appear to perform better regardless of the aim of the nozzle. In contrast, the urethral tip, which has a single nozzle port and generates a single plum stream, appears to be more sensitive to aim angle. While the urethral tip has good deposition (though by no means the best) when aimed directly at the target, its performance falls off dramatically at most other angles. We generally see with this data that multiport nozzles, which generate multiple stream plumes, perform better in off-angles compared to the single port nozzle.

The experimental results presented in the FIG. 29 demonstrate how parallel multistream plumes appear to be more resistant to plume degradation over greater distances. All nozzles can be seen to have narrow deposition zones. The single port nozzles #20 and #21 appear to degrade faster upon distance from the nozzle tip. This can especially be seen with nozzle #21. The smallest diameter single port nozzle has comparability to the multi-dose nozzles, but the constraint of this narrow port (⅕th the port area of the 0.0069 in 5 port nozzle) adversely affects the time of full dose delivery and/or the forces generated by the plume on potentially sensitive nasal membranes (see Table 2 below).

Two measured parameters, nasal model deposition and plume stability, point to a parallel multistream nozzle configuration being better able to maintain a narrow dose plume while traveling to the target. Our results demonstrate a narrow plume can deposit on the narrow recessed upper olfactory region of the human nasal sinus. Also, a multistream dose plume appears to better negotiate the intricacies of the complex human sinus. The off-angle performance advantage for a multistream dose plume compared to the urethral catheter (e.g., a single port 0.020 inch nozzle) demonstrates that clearly. Without being bound by theory, it may be that the ability of a multistream dose plume's ability to entrain air (essentially forming an air capsule) is capable of solving both of these challenges (nasal model deposition and plume stability). Such an air capsule may reduce peripheral turbulent degradation of the dose steam as well as buffer its interaction with the walls of the nasal sinus.

Table 2 addresses the property of shot duration for various narrow plume nozzles. Multi port nozzles have the advantage of initiating and completing dose delivery in relatively short times. In contrast, the best performing single port nozzle (with respect to deposition zone) required in excess of 50 milliseconds to complete a reduced volume dose. The single port nozzles would greatly limit the size of the dose that a device could deliver. A 50 μL dose would take in excess of 100 milliseconds and a 100 μL dose nearly 2/10 ths of a second. This is too long for a user actuated device. Even if increasing the single port aperture to 0.020 in, which could in theory bring the shot duration performance into line with the multiport nozzles, performance is lost, as shown in Tables 1 & FIG. 29. Alternatively, increased pressure might be able to reduce the shot time for nozzle #20, but the impact force from such a stream is more likely to be damaging to sensitive tissues.

TABLE 2

| Nozzle Name | Nozzle Description- Number of Ports & Port Diameter (inch) | Spray Deposition - Method 3 - High Speed Disk Spray Deposition zone width @ 4 cm | Fine Mist* Width @ 4 cm | Spray dose volume** in μL | Spray duration Milliseconds |
|---|---|---|---|---|---|
| #1 | 5 ports @ 0.0069 | 1.95 mm | 10.26 mm | 30 | 28.4 |
| #13 | 5 ports @ 0.0110 | 2.39 mm | 8.19 mm | 40 | 4.6 |
| #22 | 5 ports @ 0.0060 | 2.18 mm | 9.73 mm | 40 | 19.1 |
| #23 | 5 ports @ 0.0110 | 2.87 mm | 11.15 mm | 40 | 3.1 |
| #20 | 1 port @ 0.0070 | 1.36 mm | 9.09 | 26 | 56.0 |

*Each spray deposition results in some small fraction of the dose that is deposited at some distance from the central dense deposition zone. This is measurable with this method and is likely less than 10% of the dose.

TABLE 2-continued

Nozzle Description- Spray Deposition - Method 3 - High Speed Disk

| Nozzle Name | Number of Ports & Port Diameter (inch) | Spray Deposition zone width @ 4 cm | Fine Mist* Width @ 4 cm | Spray dose volume** in μL | Spray duration Milliseconds |
|---|---|---|---|---|---|

**The maximal dose load was 40 μL for this experiment. However, for those nozzles with restricted flow, less volume was required in order to measure the greatly extended duration of the spray.

Table 2 shows physical dimensions of spray plume and duration of spray for 4 parallel multiport nozzles and one single port nozzle.

Example 13

Powder Nozzles

FIG. 30 shows the effect that a bypass nozzle can make on a plume of powder as it is ejected out of a nozzle into free air. In most cases a simple tubular powder nozzle will display what is shown in FIG. 30. The front of the plume appears to form a bullet point shape. Video analysis shows that likely mechanism causing this is that the powder is ejected from the nozzle as a ballistic stream and the leading edge is immediately met by resistance from the air that it is moving into. This appears to be met by additional material fed into the back of this turbulent feature. In cases where the nozzle has clogged mid shot, the "bullet" plume essentially comes to a rest. The propagation of the plume through the ambient air requires additional force from the fresh material emanating from the nozzle.

In contrast, the bypass nozzles do not possess this feature. The powder appears to be buffered against impact with any stationary air in the firing path. Without being bound by theory, we believe that the propellant that exits the nozzle has displaced the stationary air, replacing it with a forward moving stream of gas. This forward stream of gas likely paves the way or carries the powder as if on a slipstream moving in the direction aimed. Additional studies have shown what appears to be more tightly collimated powder streams when fired from the bypass nozzles, as shown in FIG. 30.

FIG. 31 demonstrates again how the high bypass generated slipstream appears to negate the leading edge bullet point and turbulence that a simple zero bypass nozzle generates. In this case where the plumes are directed between two plates 1.8 mm apart also shows how the powder streams generated by the high bypass nozzle can remain collimated as compared to that caused by the zero bypass nozzles.

Example 14

Nozzle 18 was constructed of qty. five (5) metal tubes with an internal diameter of 0.01 inches and an external diameter of 0.02 inches contained within a 15 metal tube with an internal diameter of 0.054 inches and an external diameter of 0.070 inches. The metal tubes are frictionally secured. Air gaps are disposed between the needles. Nozzle 18 is illustrated in FIGS. 12 and 17.

Nozzle **35*b* included five (5) outlet orifices with a diameter of 0.008 inches which extend out from the housing body and terminate as sharp points. Nozzle 35*b* is illustrated in FIGS. 7, 13, and 18**.

Nozzle 31 included qty. seven (7) outlet orifices with diameter of 0.015 inches. Nozzle 31 is illustrated in FIGS. 14 and 19.

Nozzle 33 included qty. five (5) outlet orifices each with a diameter of 0.015 inches. The outlet orifices on the distal end of Nozzle 33 are illustrated in FIGS. 6 and 20.

Nozzle 17 was constructed with five outlet orifices with a diameter of 0.006 inches. The outlet orifices on the distal end of Nozzle 17 are illustrated in FIGS. 6 and 21.

Set forth in Table 3 is data generated using various nozzles in accordance with the invention.

TABLE 3

| Nozzle | Average deposition % @ 0 deg horizontal and vertical | Outlet Orifice Diameter (in) | Average Impact Force (grams) |
|---|---|---|---|
| 29 | 62% | 0.054 | 4.00 ± 0.22 |
| 18 | 58.3 | 0.054 | 4.06 ± 0.86 |
| 35B | 45.7% | 0.0075 | 2.04 ± 0.59 |
| 31 | 33.9% | 0.015 | 2.42 ± 0.37 |
| 33 | 41.6% | 0.015 | 2.32 ± 0.57 |
| 17 | 66.0% | 0.007 | 1.99 ± 0.08 |

Average deposition was done with the nozzle aimed at optimal orientation into a human nasal sinus model. Depositions were determined by dose weights deposited onto model surfaces with the average of a minimum of three experiments.

Spray plume diameter and Average impact force measurements were taken with nozzles positioned at 4 cm distant from recording device. Outlet orifice diameter is by direct measurement.

We claim:

1. A nozzle for delivering an intranasal dosage form comprising:
- a distal and a proximal end of the nozzle,
- a drug product inlet in fluid connection with the proximal end of the nozzle and configured to receive a mixture of a propellant and the intranasal dosage form,
- a nozzle body defining five channels, each of the five channels having a proximal end and a distal end, the nozzle body defining a longitudinal axis,
- a circular outlet orifice disposed at the distal end of each of the five channels forming five outlet orifices arranged in a pentagon, and
- a container containing a propellant in fluid communication with the drug product inlet, the propellant configured to propel the intranasal dosage form from the drug product inlet through the channels and out the outlet orifices,
- each of the five channels configured to generate a stream of intranasal dosage form during a delivery time course which streams form a narrow plume once exited the outlet orifices, wherein an angle of the narrow plume is about 5 degrees, about 4 degrees, about 3 degrees, about 2 degrees, about 1 degree, or about 0 degree.

2. The nozzle of claim 1 wherein the channels are disposed parallel to the longitudinal axis.

3. The nozzle of claim 1, wherein the channels are a plastic or a metal, the nozzle body is a plastic or a metal, and a void is disposed between the channels and the nozzle body.

4. The nozzle of claim 1, wherein the angle of the narrow plume is about 5 degrees.

5. The nozzle of claim 1 wherein an impact force delivered by the nozzle is decreased.

6. The nozzle of claim 1, wherein a delivery time for the intranasal dosage form is decreased.

7. The nozzle of claim 1 wherein the delivery time course is measured over a span of 4 cm from the outlet orifices.

8. The nozzle of claim 7 wherein the delivery time course is measured using high speed blotter recording.

9. The nozzle of claim 1, wherein the
narrow plume once exited the outlet orifices during the delivery time course measured 4 cm from the outlet orifices of the nozzle has a principle deposition zone of less than 3 mm.

10. The nozzle of claim 1 wherein the channels are disposed at an angle with respect to the longitudinal axis.

11. The nozzle of claim 1, wherein drug product inlet is contiguous with the proximal end of the nozzle.

12. A method for delivering a drug product to an olfactory region of a nasal cavity, the method comprising:
providing a nozzle, the nozzle having a proximal end and a distal end, a drug product inlet in fluid connection with the proximal end of the nozzle and configured to receive a mixture of a propellant and the drug product, five channels contiguous with the drug product inlet and with five circular outlet orifices arranged in a pentagon at the distal end of the nozzle, each channel for carrying the drug product;
providing a container containing a propellant in fluid communication with the drug product inlet of the nozzle, the propellant configured to propel the drug product from the drug product inlet though the channels and out the five circular outlet orifices;
providing a drug product at the drug product inlet of the nozzle; and
dispensing the propellant to propel the drug product from the drug product inlet through the channels and out the five circular outlet orifices;
wherein each of the five channels generates a corresponding stream of drug product that together form a narrow drug plume upon exiting distal end of the nozzle, wherein an angle of the narrow drug plume is about 5 degrees, about 4 degrees, about 3 degrees, about 2 degrees, about 1 degree, or about 0 degree.

13. The method of claim 12, wherein the drug product is a liquid or powder.

14. The method of claim 12, wherein the drug product inlet is contiguous with the proximal end of the nozzle.

* * * * *

UNITED STATES PATENT AND TRADEMARK OFFICE
CERTIFICATE OF CORRECTION

PATENT NO. : 9,919,117 B2  
APPLICATION NO. : 14/075126  
DATED : March 20, 2018  
INVENTOR(S) : John D. Hoekman et al.

Page 1 of 1

It is certified that error appears in the above-identified patent and that said Letters Patent is hereby corrected as shown below:

In the Claims

Column no: 16, Line(s): 45, Claim 1, "a distal and" to read as --a distal end and--.

Column no: 17, Line(s): 17, Claim 9, "principle deposition zone" to read as --principal deposition zone--.

Column no: 17, Line(s): 21, Claim 11, "wherein drug product" to read as --wherein the drug product--.

Column no: 18, Line(s): 18, Claim 12, "exiting distal end" to read as --exiting the distal end--.

Signed and Sealed this  
Eighteenth Day of September, 2018

Andrei Iancu  
*Director of the United States Patent and Trademark Office*